(12) United States Patent
Sasaki et al.

(10) Patent No.: US 6,954,274 B2
(45) Date of Patent: Oct. 11, 2005

(54) METHOD OF INSPECTING SEMICONDUCTOR INTEGRATED CIRCUIT WHICH CAN QUICKLY MEASURE A CUBIC BODY

(75) Inventors: Yoshihiro Sasaki, Tokyo (JP); Masahiko Nagao, Tokyo (JP)

(73) Assignee: NEC Electronics Corporation, Kanagawa (JP)

(*) Notice: Subject to any disclaimer, the term of this patent is extended or adjusted under 35 U.S.C. 154(b) by 451 days.

(21) Appl. No.: 10/107,824

(22) Filed: Mar. 28, 2002

(65) Prior Publication Data
US 2002/0140949 A1 Oct. 3, 2002

(30) Foreign Application Priority Data
Mar. 30, 2001 (JP) ...................................... 2001/098739

(51) Int. Cl.⁷ .............................................. G01B 11/24
(52) U.S. Cl. ...................................................... 356/606
(58) Field of Search ................................ 356/600–640, 356/237.1–237.8; 250/225

(56) References Cited

U.S. PATENT DOCUMENTS 5,877,859 A * 3/1999 Aspnes et al. ............... 356/364
6,154,281 A * 11/2000 Sentoku et al. ............. 356/401
6,424,418 B2 * 7/2002 Kawabata et al. .......... 356/445

FOREIGN PATENT DOCUMENTS

| JP | 06-103171 | 12/1994 |
| JP | 10-209227 | 8/1998 |
| JP | 11-072316 | 3/1999 |

* cited by examiner

Primary Examiner—Tu T. Nguyen
(74) Attorney, Agent, or Firm—Foley & Lardner LLP

(57) ABSTRACT

A semiconductor integrated circuit inspecting apparatus inspecting a terminal provided on a mount surface of a semiconductor integrated circuit includes a light emitter, a photographing unit and an inspector. The light emitter emits a linear light obliquely to the mount surface. The photographing unit photographs the mount surface to which the light is emitted to output a photograph signal. The inspector inspects the terminal in accordance with the photograph signal. The photographing unit has N (N is a positive integer) photographing elements. The photograph signal is outputted respectively only from M (M is a positive integer smaller than the N) photographing elements of the N photographing elements.

20 Claims, 19 Drawing Sheets

3D SENSOR MEASUREMENT PRINCIPLE

METHOD OF INSPECTING SEMICONDUCTOR INTEGRATED CIRCUIT WHICH CAN QUICKLY MEASURE A CUBIC BODY

BACKGROUND OF THE INVENTION

1. Field of the Invention

The present invention relates to an apparatus for and a method of inspecting a semiconductor integrated circuit.

2. Description of the Related Art

The following technique disclosed in Japanese Patent Publication No.6-103171 is known as a conventional apparatus for inspecting a semiconductor integrated circuit. As shown in FIG. 1, a laser beam 2 emitted by a laser oscillator 1 is inputted through a light collecting lens 3 to a scanner 4. The scanner 4 has a function of converting the collected laser beam into slit light through a cylindrical lens and the like and then deviating the slit light through a galvanomirror and the like. Thus, this apparatus is complex and expensive.

A slit light 5 outputted by the scanner 4 is emitted to a target body 6. This target body 6 is photographed by a CCD camera 7. A picture signal outputted by the CCD camera 7 is converted into a one-bit digital picture signal by an A/D converter 8. A picture signal outputted by the A/D converter 8 is stored in a picture memory 9 in accordance with an instruction from a CPU 12, and it is simultaneously inputted to an address detecting circuit 11, which detects an address when picture information is maximum for each horizontal scan.

FIG. 2 shows the content of the picture memory 9. As shown in FIG. 2, in horizontal h pixels and vertical v pixels, each pixel is configured at one bit. An address in a horizontal direction is represented by i (i=1 to h), and an address in a vertical direction is represented by j (j=1 to v). This picture memory 9 is configured such that visual information of the CCD camera 7 is arrayed as two dimensions, and it corresponds to each CCD element.

In the above-mentioned explanation, the target body 6 may be BGA (Ball Grid Array) or CSP (Chip Size Package).

As shown in FIGS. 3A, 3B, the BGA is configured such that connection units (gold pads) are aligned on a mount surface 51a of an IC chip 51 longitudinally and laterally, and solder balls 52, 53 . . . are placed on the respective connection units. In this BGA, the solder balls 52, 53 . . . aligned on the mount surface 51a of the IC chip 51 are fused and bonded on lands of a substrate, and the surface mounting operation is carried out.

Also, the CSP is configured such that a plurality of solder balls are aligned on the mount surface of the IC chip longitudinally and laterally, similarly to the BGA. As shown in FIG. 4, the CSP is configured so as to be sealed by a resin mold 62 in the size substantially similar to that of an IC chip 61 (real chip size package) and solder balls 63, 64 . . . are placed through respective bumps B on the connection units of the IC chip 61. In this CSP, similarly to the BGA, the solder balls 63, 64 . . . aligned on a mount surface 61a of the IC chip 61 are fused and bonded on the lands of the substrate, and the surface mounting operation is carried out.

As mentioned above, when the plurality of solder balls are placed on the mount surface of the IC chip and those solder balls are used to carry out the surface mounting operation, the connection units of the IC chip are typically composed of one row or two or more rows. Thus, the solder balls are placed in a shape of rows.

A light cutting method used to measure a cubic body, such as a solder ball or the like, will be described below.

As shown in FIG. 5, a plurality of BGA type IC chips 102 are placed on a JEDEC tray 101. The IC chip 102 is set such that its mount surface 102a is located uprightly. A plurality of solder balls 103 aligned on the mount surface 102a longitudinally and laterally are inspected.

The inspection of the solder ball 103 includes the inspections of a shape, a height, a solder amount (ball volume), a position and a coplanarity of a bump.

The coplanarity typically implies a floating amount of a terminal from a ground that is formed by a package terminal. It is represented by a distance between each terminal when a surface mount package is placed on a flat plane and the mount plane. If this distance is too long, it is impossible to sufficiently fill solder between the terminal and a foot print of a mount substrate when the surface mounting operation is done. Thus, there may be a case that the solder bonding is imperfect. The coplanarity is the dimension, from which the reliability and the yield of the solder boding is determined, in the package on which the surface mounting operation is performed. In particular, a value at which the distance between each terminal and the mounted plane is maximum is important.

In the BGA representing an area array package, the yield in the size of the solder ball forming the sealant of the package and the curvature and the terminal of the substrate has influence on the coplanarity. In order to inspect the coplanarity of the IC chip, as a rule, it is necessary to measure the heights of all solder balls in the IC chip.

A linear light emitter 104 obliquely emits a linear light L to the mount surface 102a of the IC chip 102. The linear light L scans the solder balls 103 for each row. The linear light emitter 104 is designed so as to carry out a reciprocating motion in order to scan the mount surface 102a of the IC chip 102 through the linear light L. Thus, as shown in FIG. 6, the linear light L obliquely emitted to the mount surface 102a of the IC chip 102 by the linear light emitter 104 is scanned in an X-direction indicated by an arrow in FIG. 6, along the mount surface 102a.

Here, the linear light L may be, for example, a laser light. Also, the linear light L may be the lights in which the lights emitted from a light source, such as a light emission diode (LED) or the like, are converged through a cylindrical lens into linear lights.

As shown in FIG. 5, a photographing unit 105 for photographing a changing picture of the linear light L is placed directly over the mount surface 102a of the IC chip 102 so that it is located opposite to the mount surface 102a. The photographing unit 105 is, for example, the CCD camera. The photographing unit 105 is fixed.

The photographing unit 105 is fixed, and it is not shifted together with the scanning (the arrow X of FIG. 6) of the linear light L. Thus, as shown in FIG. 6, the photographing unit 105 has the photographing range in which when the linear light L is scanned in the X-direction along the mount surface 102a and the light is emitted to the solder balls 103 in a plurality of rows, all of the solder balls 103 in the plurality of rows can be covered.

An operational process is performed on the picture information photographed by the photographing unit 105, and the heights of the respective solder balls 103 are detected. Here, for example, the following methods can be used in order to detect the heights of the respective solder balls 103, on the basis of the picture information of the photographing unit 105.

As shown in FIG. 7, if a distortion amount of the linear light L is assumed to be I and an emission angle of the linear light emitter 104 is assumed to be θ, a protrusion height h of each solder ball 103 is represented by h=I tan θ. The distortion amount I of the linear light L is changed in the process in which the linear light L scans the respective rows of the solder balls 103 in the plurality of rows.

As mentioned above, in the light cutting method, the linear light L is obliquely emitted to the mount surface 102a of the IC chip 102, and this linear light L is scanned on the mount surface 102a on which the solder balls 103 are placed. Then, the fact that the linear light L is distorted proportionally to the mount height (protrusion height h) of the solder ball 103 during the scanning is used to perform the operational process on the changing picture information of the linear light L, for example, by using the equation of h=I tan θ. Accordingly, the height of each solder ball 103 is measured.

Thus, it is possible to inspect the allowance or rejection of the plurality of solder balls 103 aligned on the mount surface 102a of the IC chip 102 easily and surely. In particular, it is possible to accurately measure the mount height h of the solder ball 103, and possible to provide this method for the inspection of the coplanarity.

By the way, Japanese Laid Open Patent Application (JP-A-Heisei 10-209227) discloses the following method of inspecting a semiconductor integrated circuit. In the method of inspecting a semiconductor integrated circuit, which inspects a plurality of solder balls aligned on a mount surface of a semiconductor integrated circuit longitudinally and laterally, a linear light emitter obliquely emits a linear light to the mount surface, and scans the solder balls for each row, and a photographing unit photographs a changing picture of the linear light during the scanning, and a picture processor performs an operational process on the photographed picture information, and then detects a height of each solder ball. The operational process of the picture process is carried out by using the equation represented by a protrusion height h=I tan θ, when a distortion amount of the linear light is assumed to be I and an emission angle is assumed to be θ.

Japanese Laid Open Patent Application (JP-A-Heisei 11-72316) discloses the following apparatus for measuring a flatness of an IC lead. This apparatus is provided with: a slit plate having a plurality of linear slits for light transmission, which are arrayed at an identical interval in parallel to each other; a parallel light flux light source for emitting a parallel light flux to the slit plate from the inclined direction at the same angle on an opposite side along the array direction of the linear slit with respect to a normal line of the slit plate; a work stage for holding an IC package targeted for the measurement at a position on a light emission side of the slit plate so that the formation plate of the lead ball is parallel to the slit plate; a photographing unit for photographing the surfaces of the respective lead balls arrayed on the lead ball formation plane; and a measuring unit for determining a distance between centers of light arrival points formed on the surfaces of the respective lead balls on the basis of the picture generated by the photographing unit and then measuring the flatness of each lead ball in accordance with the distance between the centers.

As mentioned above, in the light cutting method, the entire shape and size (height) of each bump are recognized on the basis of the distortion amount I and the emission angle θ of each linear light L, when the linear light L is emitted to a different height of each bump a plurality of times, in the process in which the linear light L scans each bump.

As mentioned above, the reason why a plurality of photograph pictures with regard to each bump are generated by emitting the linear light L to a plurality of positions at the different heights in each bump is that an apex position in the bump is not always known in advance so as to determine the height of the entire bump.

That is, the maximum value of the heights obtained from each of the plurality of photograph screens with regard to each bump is assumed to be the height of the entire bump.

In this way, it is necessary to perform the photographing operation on each bump a plurality of times. Thus, in order to make the measuring time shorter, a time required to carry out each photographing operation (a time required to obtain one picture) is desired to be shorter.

SUMMARY OF THE INVENTION

The present invention is accomplished in view of the above mentioned problems. Therefore, an object of the present invention is to provide an apparatus for and a method of inspecting a semiconductor integrated circuit, which can quickly measure a cubic body.

Another object of the present invention is to provide an apparatus for and a method of inspecting a semiconductor integrated circuit, in which a time required to obtain a photograph picture of a cubic body is short, a cubic structure is simple, and a cheap measurement can be quickly carried out.

Still another object of the present invention is to provide an apparatus for and a method of inspecting a semiconductor integrated circuit, in which a scanning time of a photographing unit to obtain a photograph picture of a cubic body is short and the cubic body can be quickly measured.

Still another object of the present invention is to provide an apparatus for and a method of inspecting a semiconductor integrated circuit, in which even if there is a trouble, such as a curvature and the like, in a carrying unit (a tray) of a cubic body or a feeding unit (a feeding tray) or a package (packing) unit, a bad influence caused by the trouble can be automatically solved.

Still another object of the present invention is to provide an apparatus for and a method of inspecting a semiconductor integrated circuit, in which even if there is a trouble, such as a curvature and the like, in a carrying unit of a cubic body or a feeding unit or a package unit, a bad influence caused by the trouble can be solved at a real time.

Still another object of the present invention is to provide an inspecting apparatus having a simple configuration.

In order to achieve an aspect of the present invention, a semiconductor integrated circuit inspecting apparatus inspecting a terminal provided on a mount surface of a semiconductor integrated circuit, includes: a light emitter emitting a linear light obliquely to the mount surface; a photographing unit photographing the mount surface to which the light is emitted to output a photograph signal; an inspector inspecting the terminal in accordance with the photograph signal, and wherein the photographing unit has N (N is a positive integer) photographing elements, and wherein the photograph signal is outputted respectively only from M (M is a positive integer smaller than the N) photographing elements of the N photographing elements.

In this case, only the scanning lines corresponding to the M photographing elements of the N photographing elements are scanned such that the photographing unit outputs the photograph signals.

Also in this case, the photographing unit has N (=n lines×l rows) (n and l are positive integers, respectively) photographing elements, and wherein only the scanning lines corresponding to M (=m×l rows) (m is a positive integer smaller than the n) photographing elements of the photographing elements of n lines×l rows are scanned such that the photographing unit outputs the photographing signals.

Further in this case, the light emitter and the photographing unit constitutes a sensor, and wherein when regions on the mount surface to which the light is emitted are changed, one of the sensor and the semiconductor integrated circuit is relatively shifted with respect to the other one of the sensor and the semiconductor integrated circuit such that the M photographing elements can photograph the regions to which the light is emitted.

In this case, The semiconductor integrated circuit inspecting apparatus, further includes: a calculator calculating a height of the mount surface, in accordance with the photograph signal.

Also in this case, the calculator determines a relation between the number of dots indicative of the emission of the light and a position in a height direction of the semiconductor integrated circuit, in a photograph picture photographed by the M photographing elements to calculate a height of the mount surface, in accordance with the relation.

Further in this case, the semiconductor integrated circuit inspecting apparatus further includes: a first controller controlling a distance between the sensor and the semiconductor integrated circuit, and wherein the first controller controls the distance in accordance with the calculated height of the mount surface.

In this case, the first controller controls the distance such that the M photographing elements can photograph the mount surface to which the light is emitted, when the height of the mount surface is changed.

Also in this case, the semiconductor integrated circuit inspecting apparatus further includes: a second controller controlling the photographing elements such that the M photographing elements outputting the photograph signals of the N photographing elements are changed, and wherein the second controller controls the photographing elements such that the M photographing elements are changed, in accordance with the calculated height of the mount surface.

Further in this case, when the positions of the mount surface to which the light is emitted are changed from a first position to a second position, the photograph signals in which the first position is photographed are outputted only from a first photographing element group of the M photographing elements of the N photographing elements, and the photograph signals in which the second position is photographed are outputted only from a second photographing element group of the M photographing elements different from the first photographing element group of the N photographing elements.

In this case, the photographing element is a CMOS photographing element or a CCD photographing element.

Also in this case, CMOS photographing elements or CCD photographing elements of the N are arranged in a shape of a matrix composed of p lines and q rows (each of p and q is a positive integer), and wherein the photograph signals are outputted only from the CMOS photographing elements or CCD photographing elements in a range of (p-α) lines and (q-β) rows (the α is a positive integer smaller than the p, and the β is a positive integer smaller than the q).

Further in this case, an angle between an optical axis of the light emitter and an axis line of the photographing unit is about 90 degrees.

In this case, the axis line of the photographing unit substantially coincides with an optical axis of a light reflected from the mount surface to which the light is emitted.

Also in this case, the semiconductor integrated circuit inspecting apparatus further includes: a two-dimensional measurement photographing unit photographing a flat shape of the mount surface; and a shifting unit shifting the two-dimensional measurement photographing unit and the sensor with respect to the semiconductor integrated circuit.

Further in this case, the semiconductor integrated circuit is a BGA, and wherein the terminal is a solder ball, and wherein the inspector measures a height of the solder ball in accordance with the photograph signal.

In order to achieve another aspect of the present invention, a method of inspecting a semiconductor integrated circuit, which inspects a terminal provided on a mount surface of a semiconductor integrated circuit, includes: (a) providing a photographing unit having N (N is a positive integer) photographing elements; (b) detecting a position of the terminal on the mount surface; (c) obliquely emitting a linear light to the mount surface; (d) relatively shifting an emission target of the light and the mount surface at a set speed such that the light is emitted to each of a plurality of positions of the mount surface; (e) photographing by the photographing unit a region on the mount surface to which the light is emitted to output a photograph signal from the photographing unit; and (f) inspecting the terminal in accordance with the photograph signal, and wherein a plurality of the photograph signals is outputted from only M (M is a positive integer smaller than the N) photographing elements of the N photographing elements, and wherein the set speed when the light is emitted to the terminal is set to be higher as compared with a case when the light is not emitted to the terminal, based on a result of the (b).

In order to achieve still another aspect of the present invention, a method of inspecting a semiconductor integrated circuit, which inspects a terminal provided on a mount surface of a semiconductor integrated circuit, includes: (g) providing N (N is a positive integer) CMOS photographing elements or CCD photographing elements arranged in a shape of a matrix composed of p lines and q rows (each of p and q is a positive integer); (h) detecting a position of the terminal on the mount surface; (i) obliquely emitting a linear light to the mount surface; (j) photographing by the photographing unit a region on the mount surface to which the light is emitted to output the photograph signal from the photographing unit; and (k) inspecting the terminal in accordance with the photograph signal, and wherein a plurality of the photograph signals are outputted from only M (M is a positive integer smaller than the N) CMOS photographing elements or CCD photographing elements in a range of (p-α) lines and (q-β) rows (the α is a positive integer smaller than the p, and the β is a positive integer smaller than the q) of the N CMOS photographing elements or CCD photographing elements, and wherein the range of the (p-α) lines and (q-β) rows is set to include a single one of the terminal in accordance with the result of the (h).

In this case, a combination of the (c), (d), (e) and (f) constitutes the light cutting method.

Also in this case, a combination of the (i), (j) and (k) constitutes the light cutting method.

In order to achieve yet still another aspect of the present invention, a method of inspecting a semiconductor integrated circuit, includes: fixing a two-dimension measuring camera and a three-dimension measuring camera on a XY stage, and measuring a sample by using the two-dimension measuring camera and the three-dimension measuring camera.

By the way, traditionally, an inspector based on a scanning type laser deviation indicator using an AO element or a galvano-mirror, a detection width is limited to a range of several mm. However, the actual usage of a high speed detection element having about 2000×2000 pixels enables a scan width at one scanning to be increased to 10 to 20 mm. Thus, it is possible to improve a detection speed per unit area.

DESCRIPTION OF THE PREFERRED EMBODIMENTS

An embodiment of the present invention will be described below with reference to the attached drawings.

Figure 1:
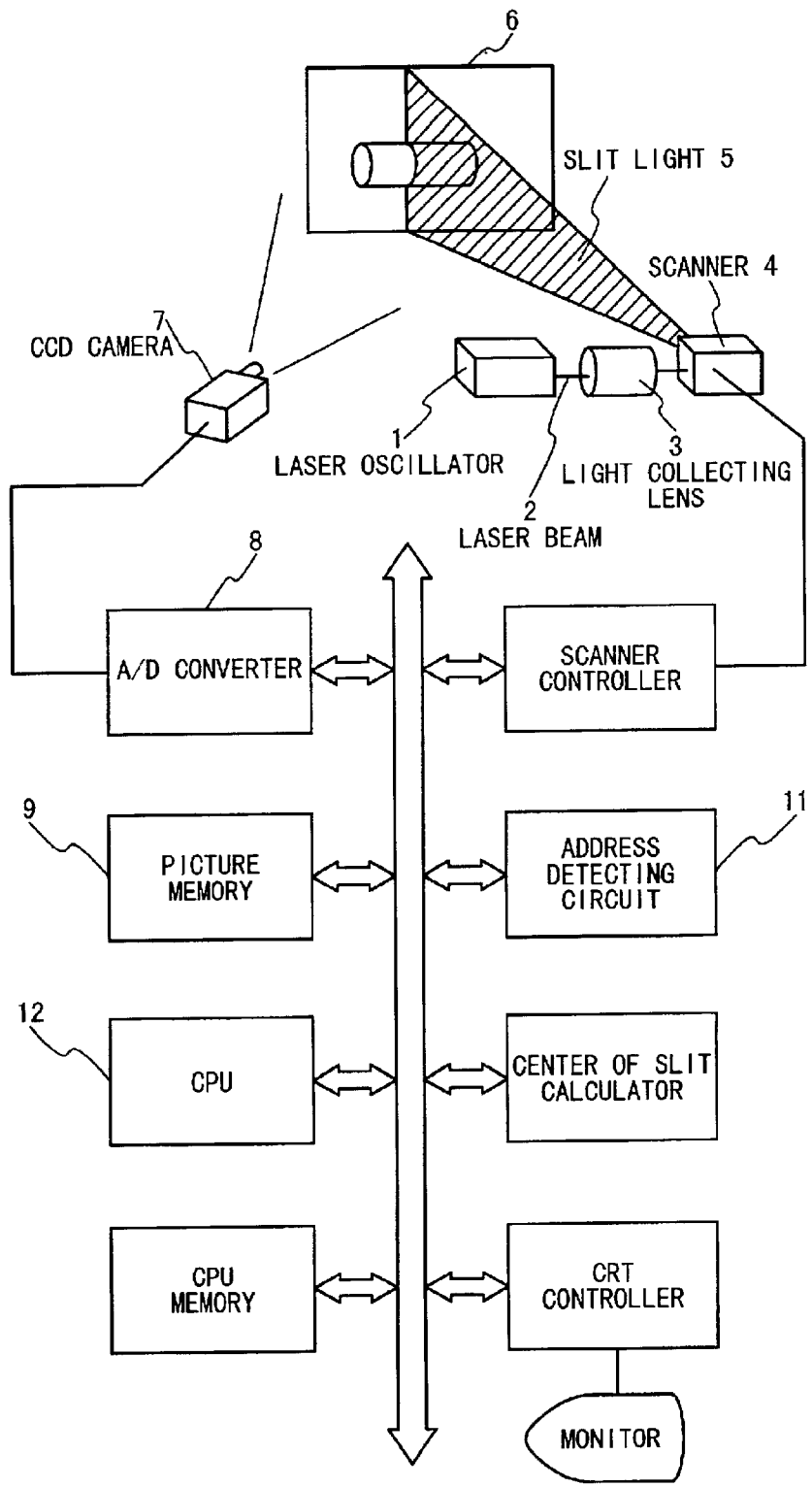
FIG. 1 is a block diagram showing a configuration of a conventional apparatus for inspecting a semiconductor integrated circuit.
Figure 2:
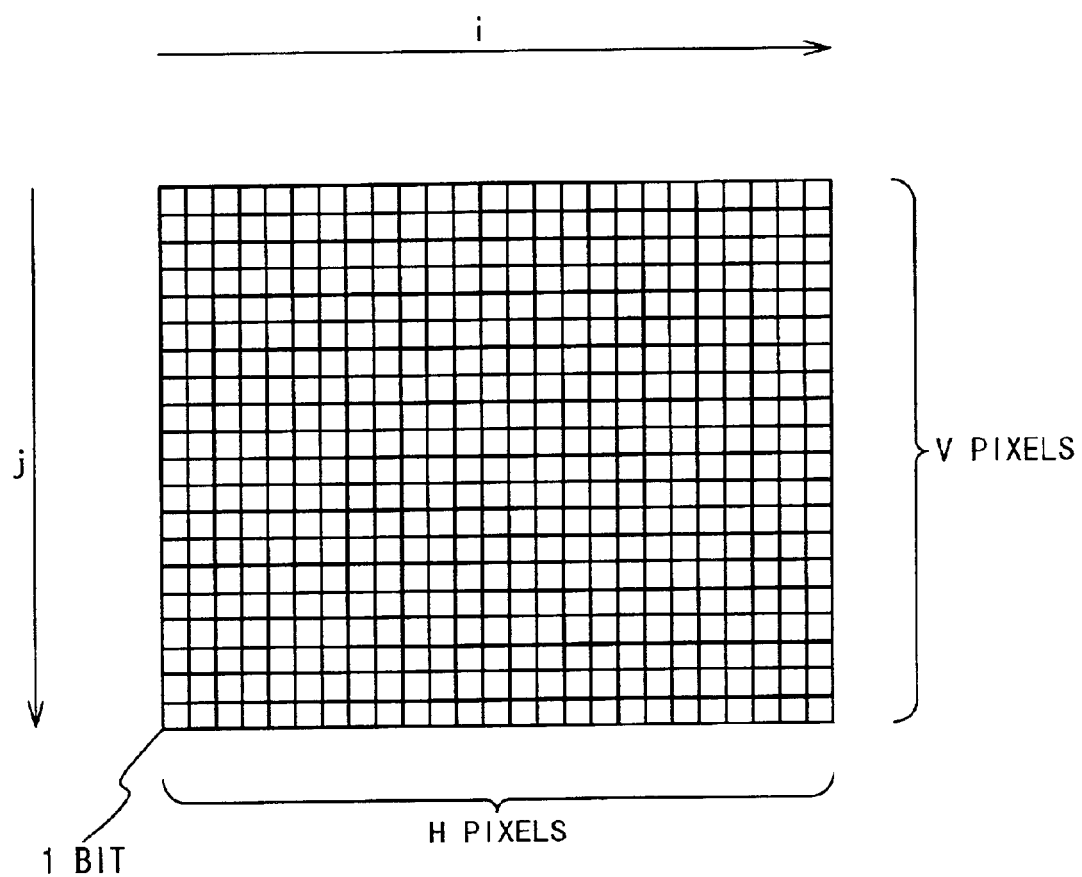
FIG. 2 is a view showing a picture memory used in a conventional apparatus for inspecting a semiconductor integrated circuit.
Figure 3A:
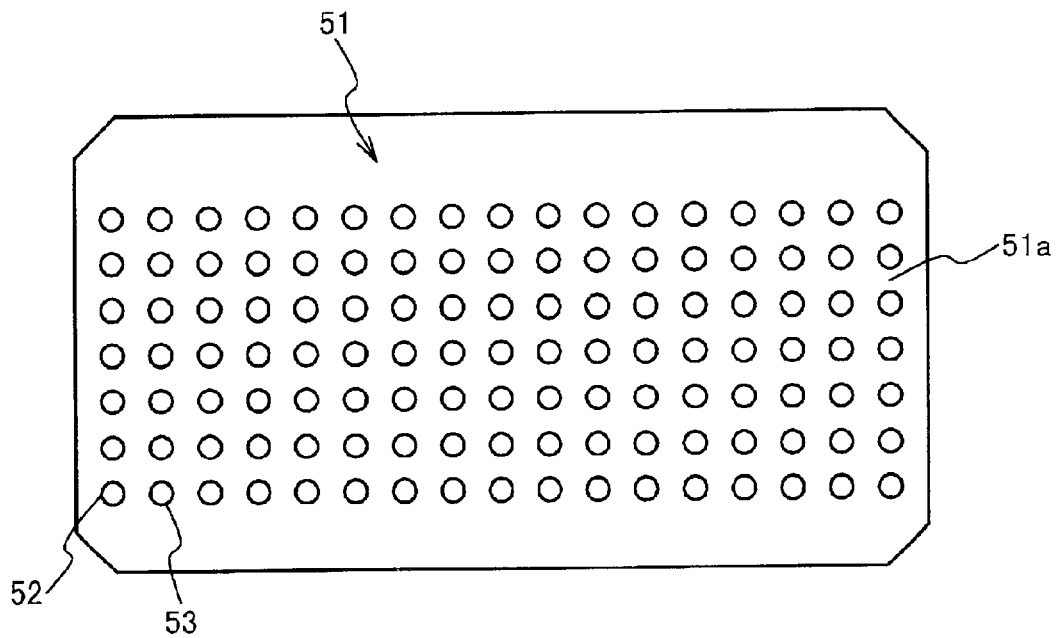
FIG. 3A is a plan view showing a conventional typical BGA.
Figure 3B:
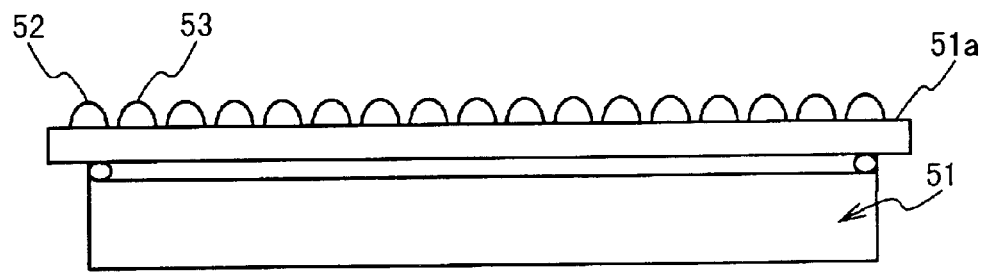
FIG. 3B is a side view showing the conventional typical BGA.
Figure 4:
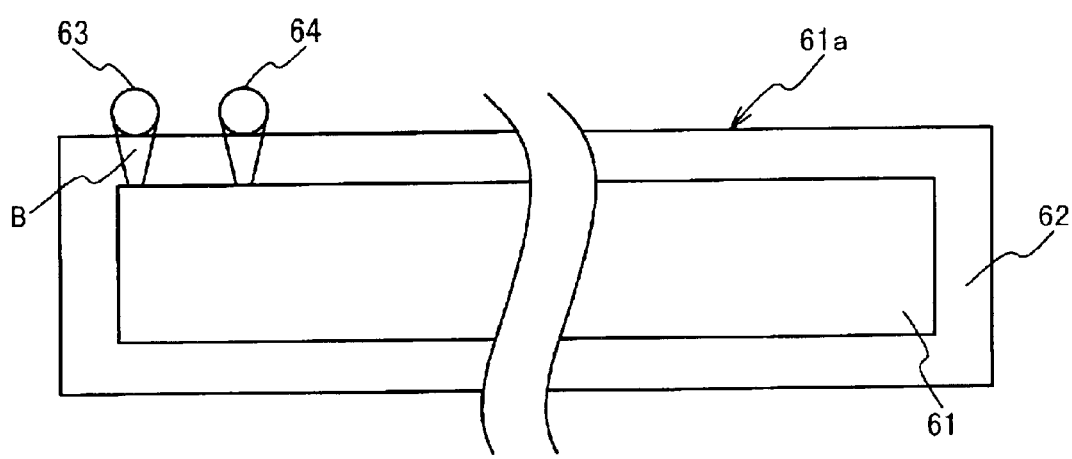
FIG. 4 is a side view showing a conventional typical CSP.
Figure 5:
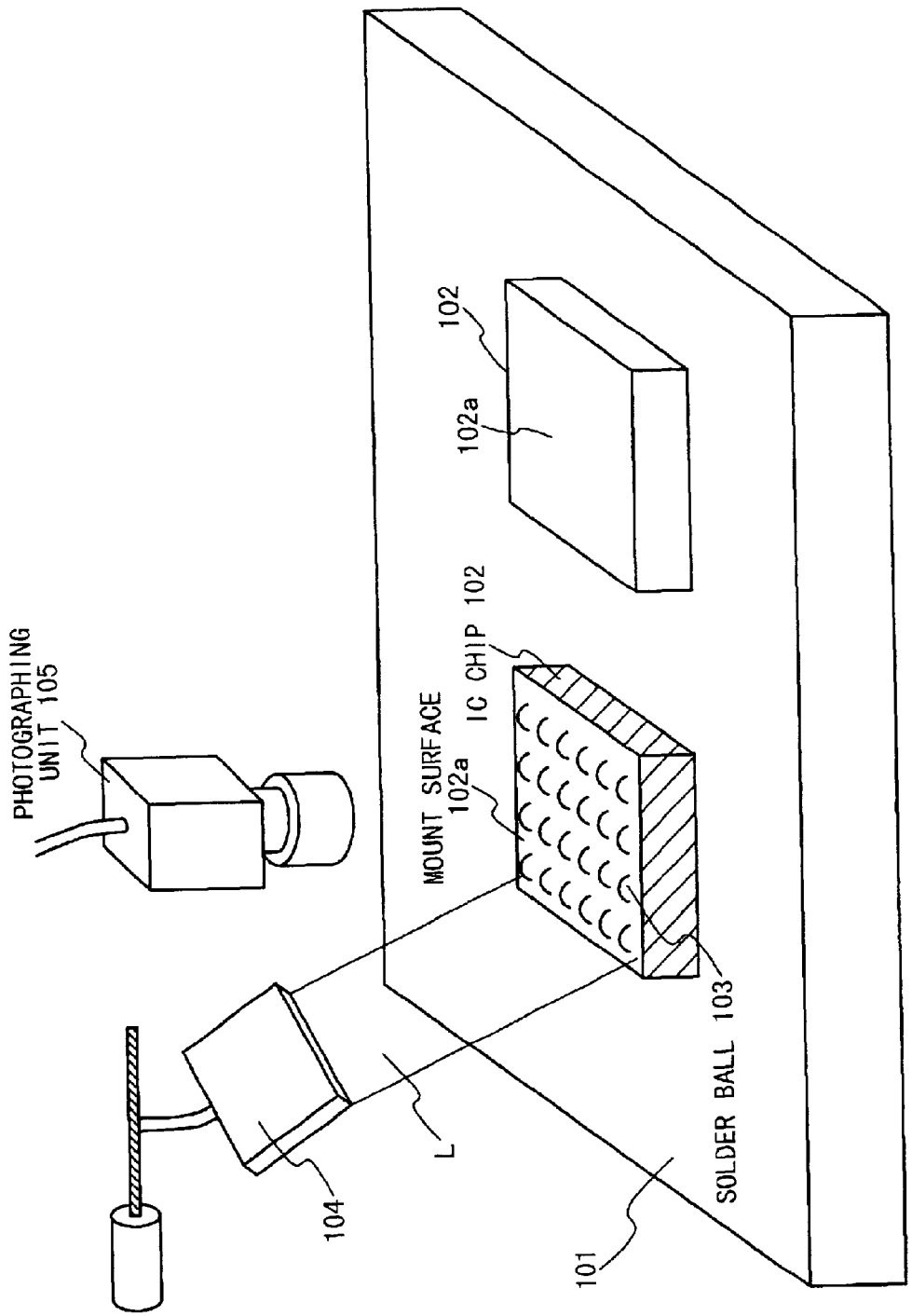
FIG. 5 is a perspective view showing a configuration of a conventional another apparatus for inspecting a semiconductor integrated circuit.
Figure 6:
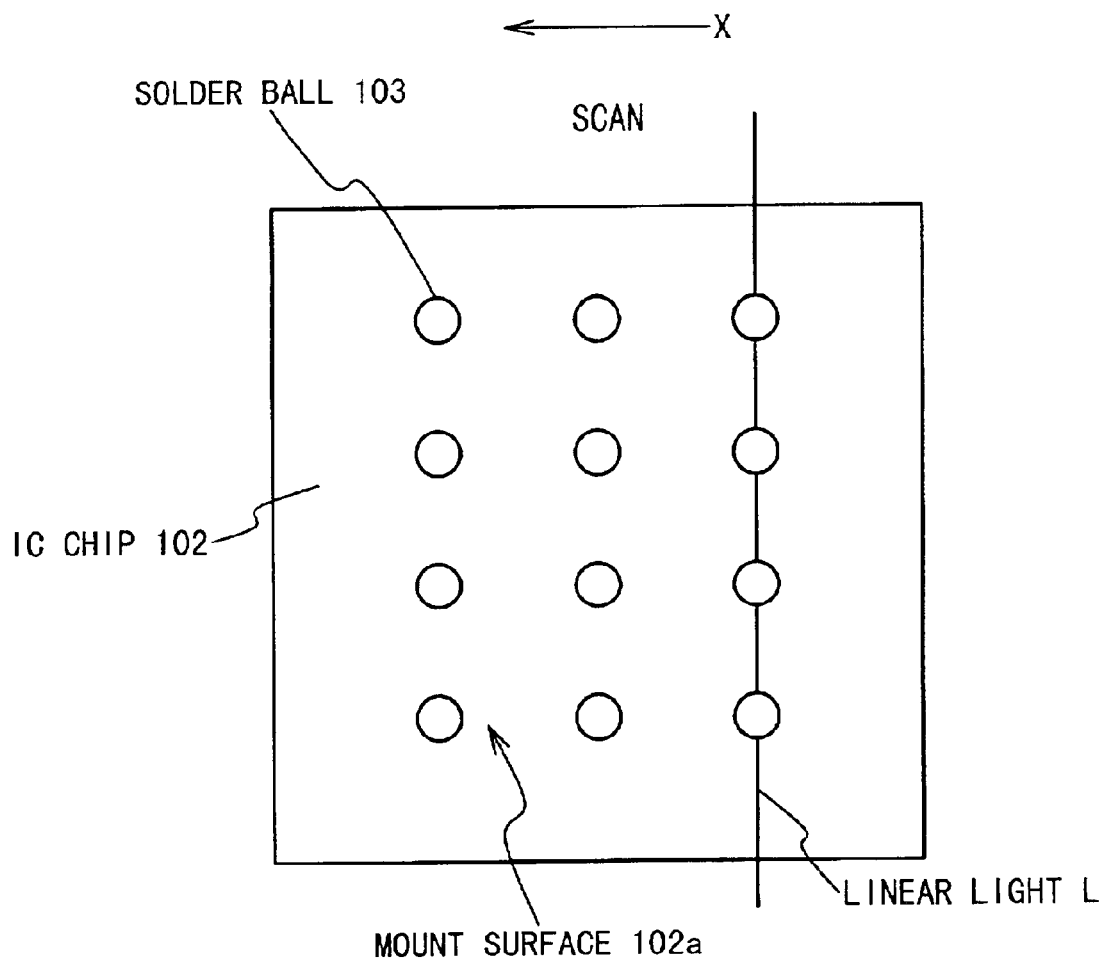
FIG. 6 is a plan view showing a scanning direction when a linear light scans a mount surface, in the conventional another apparatus for inspecting a semiconductor integrated circuit.
Figure 7:
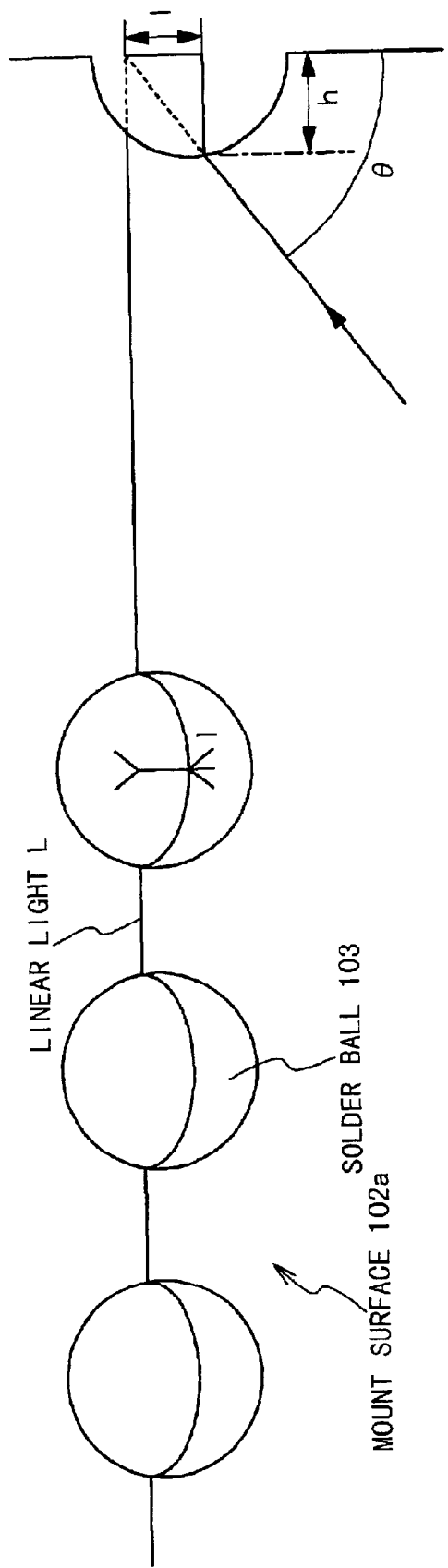
FIG. 7 is a view describing a method of determining a height of a solder ball, in accordance with a linear light emitted to a solder ball, in the conventional another apparatus for inspecting a semiconductor integrated circuit.
Figure 8:
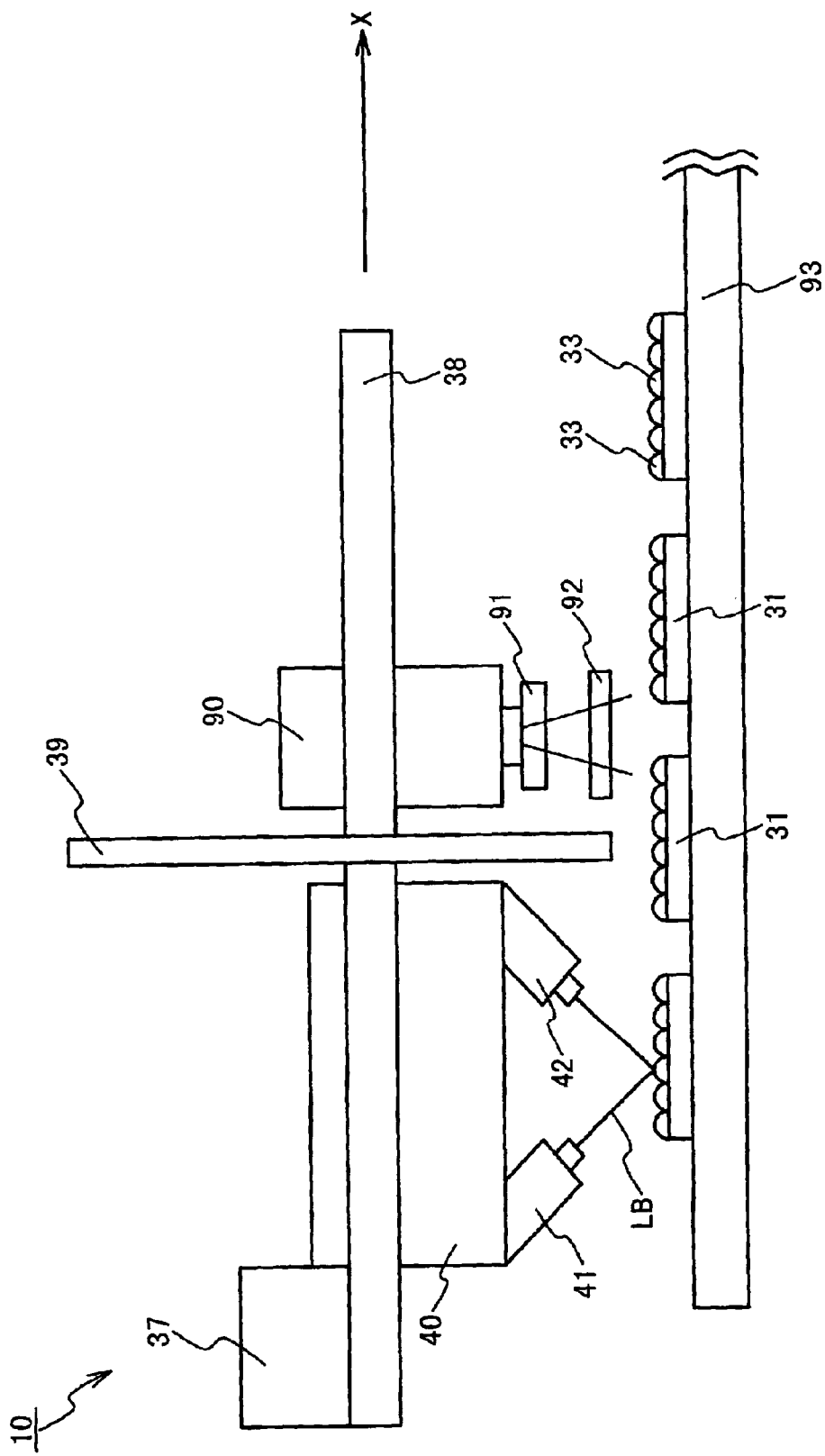
FIG. 8 is a side vies diagrammatically showing an entire configuration of an embodiment of an apparatus for inspecting a semiconductor integrated circuit of the present invention.

As shown in FIG. 8, an inspecting apparatus 10 of a semiconductor integrated circuit in this embodiment is used, for example, for inspecting solder balls (bumps) 33 of a plurality of BGA type IC chips 31 placed on a tray 93.

The inspecting apparatus 10 of the semiconductor integrated circuit is provided with: a laser sensor 40 for carrying out a three-dimension (3D) measurement; an IC appearance inspection CCD camera sensor 90 for carrying out a two-dimension (2D) measurement; and an XY table (not shown) for shifting the laser sensor 40 and the CCD camera sensor 90 at a high accuracy. The inspecting apparatus 10 has a laser light source 41 and a CCD sensor 42.

This embodiment is configured such that the XY table is used to shift the laser sensor 40 and the CCD camera sensor 90 and then fix a tray 93 on which the IC chip 31 is placed. Here, instead of this configuration, it may be designed such that the laser sensor 40 and the CCD camera sensor 90 are fixed and the XY table is used to shift the tray 93. That is, the laser sensor 40 and the CCD camera sensor 90 and the IC chip 31 may be relatively shifted. Thus, any of them may be shifted.

As this laser light source 41, the source is used which can emit a laser beam LB having a shape of slit, in which a width is about 10 to 20 $\mu$m.

By the way, in this embodiment, the device for emitting the linear light, such as the laser beam LB or the like, is not limited to the laser light source 41. The linear light may be, for example, the light in which lights emitted from a light source, such as a light emission diode (LED) or the like, is converged through a cylindrical lens to the linear light.

A symbol 37 denotes a Y stage of the XY table, a symbol 38 denotes an X stage of the XY table, and a symbol 39 denotes a partition.

Figure 9:
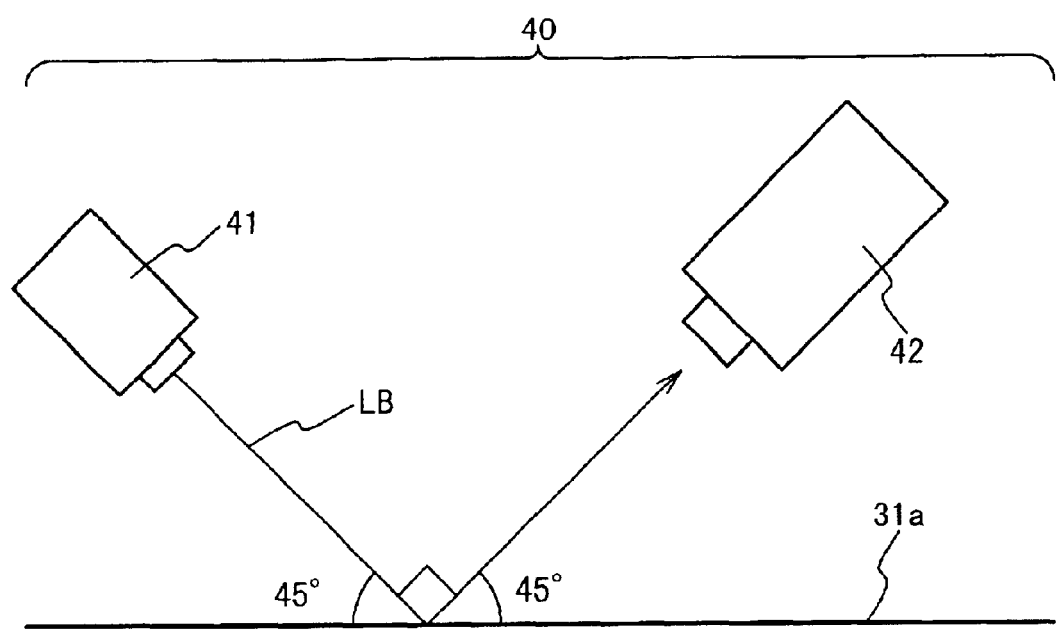
FIG. 9 is a side view showing a positional relation between a laser light source, a CCD sensor and a mount surface, in an embodiment of an apparatus for inspecting a semiconductor integrated circuit of the present invention.

As shown in FIG. 9, the laser light source 41 is placed at a position at which the laser beam LB is inputted to a substrate surface 31a of the IC chip 31 or the solder ball 33 at an angle of 45 degrees. The CCD sensor 42 of the laser sensor 40 is placed at a position at which the lights reflected at a reflection angle of 45 degrees from the substrate surface 31a of the IC chip 31 or the solder ball 33 can be photographed from its direct rear. Due to this arrangement condition, an angle between an optical axis of the laser light source 41 and an axis line of the CCD sensor 42 is 90 degrees.

Since the angle between the optical axis of the laser light source 41 and the axis line of the CCD sensor 42 is 90 degrees, a height difference of a plane cut by a slit light can be made the highest, which enables the resolution in a height direction of a measurement target of the CCD sensor 42 to be maximum.

Also, the CCD sensor 42 of the laser sensor 40 is placed at the position at which the lights reflected from the substrate surface 31a of the IC chip 31 or the solder ball 33 can be photographed from its direct rear. Thus, the detection property on a flat plane at an apex of the solder ball 33 is improved since a reflection amount (a light amount) of the reflection lights on the flat plane at the apex becomes stronger. An optical axis of the lights reflected from the substrate surface 31a of the IC chip 31 or the solder ball 33 coincides with the axis line of the CCD sensor 42.

The positional relation (arrange condition) between the laser light source 41 and the CCD sensor 42 that is shown in FIG. 9 is held and shifted without any change, even if the laser light source 41 and the CCD sensor 42 are shifted by the XY table when it is measured.

The CCD sensor 42 carries out a partial scan, as described later. This CCD sensor 42 uses an electronic shutter. Thus, it is not necessary to stop the CCD sensor 42 for each frame. Hence, data can be obtained at a high speed, which contributes to the improvement in a throughput.

The CCD camera sensor 90 for carrying out the 2D measurement employs a TDI (Time Delay Integration) method. According to this method, similarly to the CCD sensor 42 of the laser sensor 40, it is not necessary to stop the camera for each frame. Thus, the data can be obtained at the high speed, which contributes to the improvement in the throughput. The simultaneous usage of oblique light ring illumination captures a minute picture, and a picture process is performed on it. Hence, it is possible to measure a diameter of a ball and a position of the ball and also detect a presence or absence of the ball, a shape of the ball, a crack of the ball at a high accuracy. In FIG. 8, a symbol 91 denotes upward illumination, and a symbol 92 denotes side illumination.

The XY table is assembled on a stone base and floated by an air bearing. An encoder mounted on the XY table reads out values at measurement points X, Y of the laser sensor 40 and the CCD camera sensor 90.

The laser sensor 40 for the 3D measurement and the CCD camera sensor 90 for the 2D measurement are placed on the same stage. Then, the shift of the stage enables the 3D measurement and the 2D measurement to be carried out at one time for a plurality of IC chips 31.

In this apparatus 10, a later-described idea enables a detecting mechanism of the laser sensor 40 to be simpler than that of a conventional mechanism. Thus, the CCD camera sensor 90 and the laser sensor 40 can be placed on the same stage. Hence, a scanner is unnecessary, which results in a drop in a price of the apparatus 10.

Also, as shown in FIG. 8, a partition 39 having a high light shield property is placed between the laser sensor 40 and the CCD camera sensor 90. This placement can cancel the mutual influence between the 3D measurement illumination and the 2D measurement illumination.

The measurement principle of the laser sensor 40 for the 3D measurement will be described below with reference to FIGS. 10A to 11C.

Figure 10A:
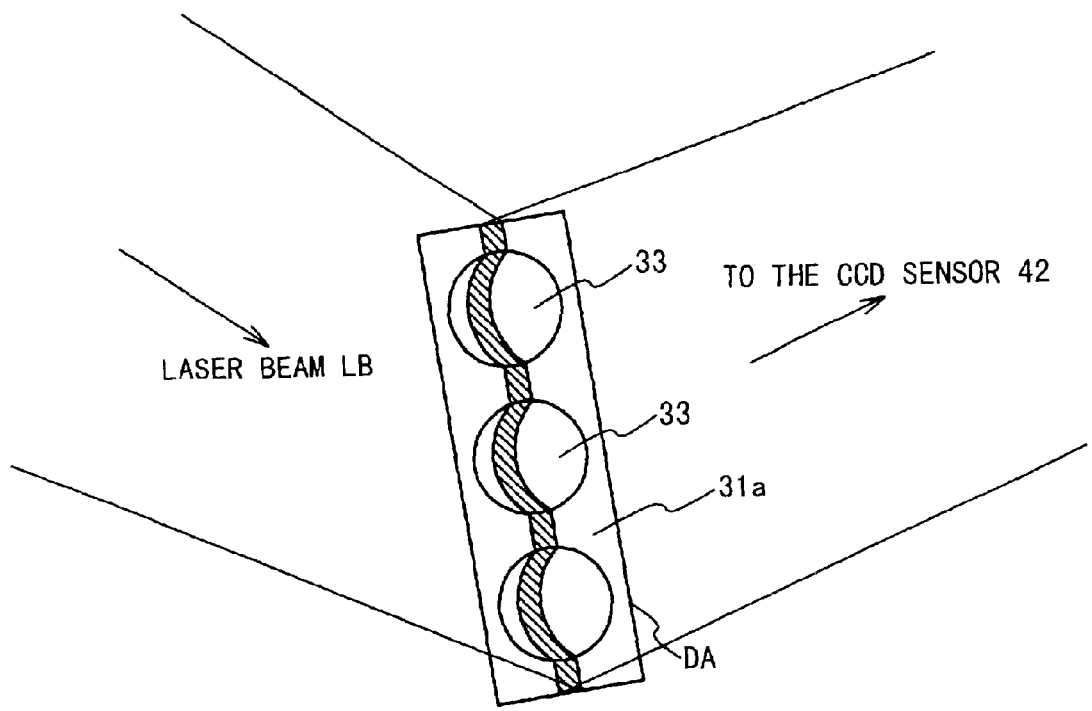
FIG. 10A is a perspective view diagrammatically showing a manner when a solder ball to which a laser beam is emitted is photographed by a CCD sensor, in an embodiment of an apparatus for inspecting a semiconductor integrated circuit of the present invention.
Figure 11A:
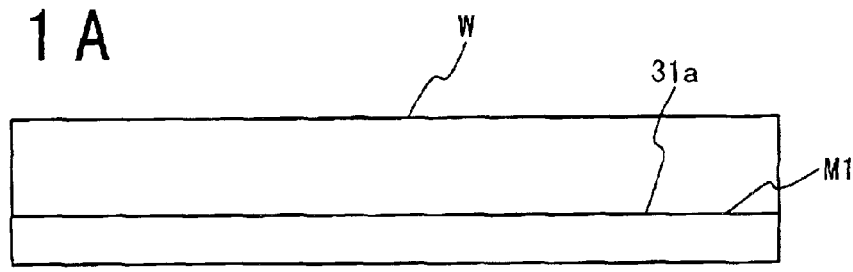
FIG. 11A is a photograph picture when a laser beam is emitted to only a mount surface, in an embodiment of an apparatus for inspecting a semiconductor integrated circuit of the present invention.
Figure 11B:
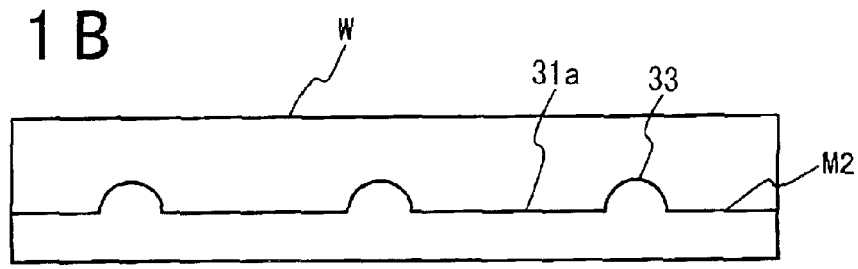
FIG. 11B is a photograph picture when a laser beam is emitted to a lower position in height in a solder ball.
Figure 11C:
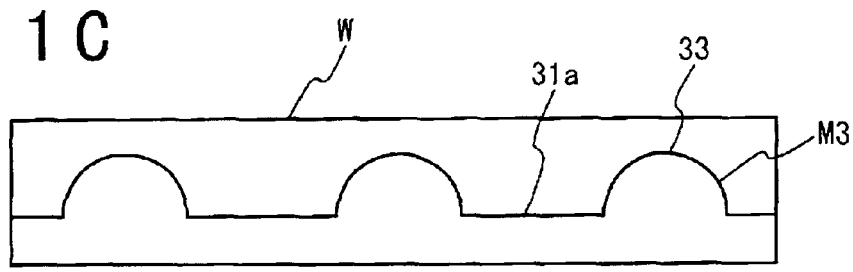
FIG. 11C is a photograph picture when the laser beam is emitted to a higher position in height in the solder ball.

As shown in FIG. 10A, the laser beam LB in the shape of slit, which has a slight width and is emitted from the laser light source 41, is emitted onto the surface of the solder ball 33, or it is emitted to the substrate surface 31a of the IC chip 31 in a situation where there is no solder ball. In FIG. 10A, a symbol DA denotes a detection area resulting from the CCD sensor 42. FIGS. 11A to 11C show the pictures corresponding to the detection area DA of the CCD sensor 42.

Figure 12:
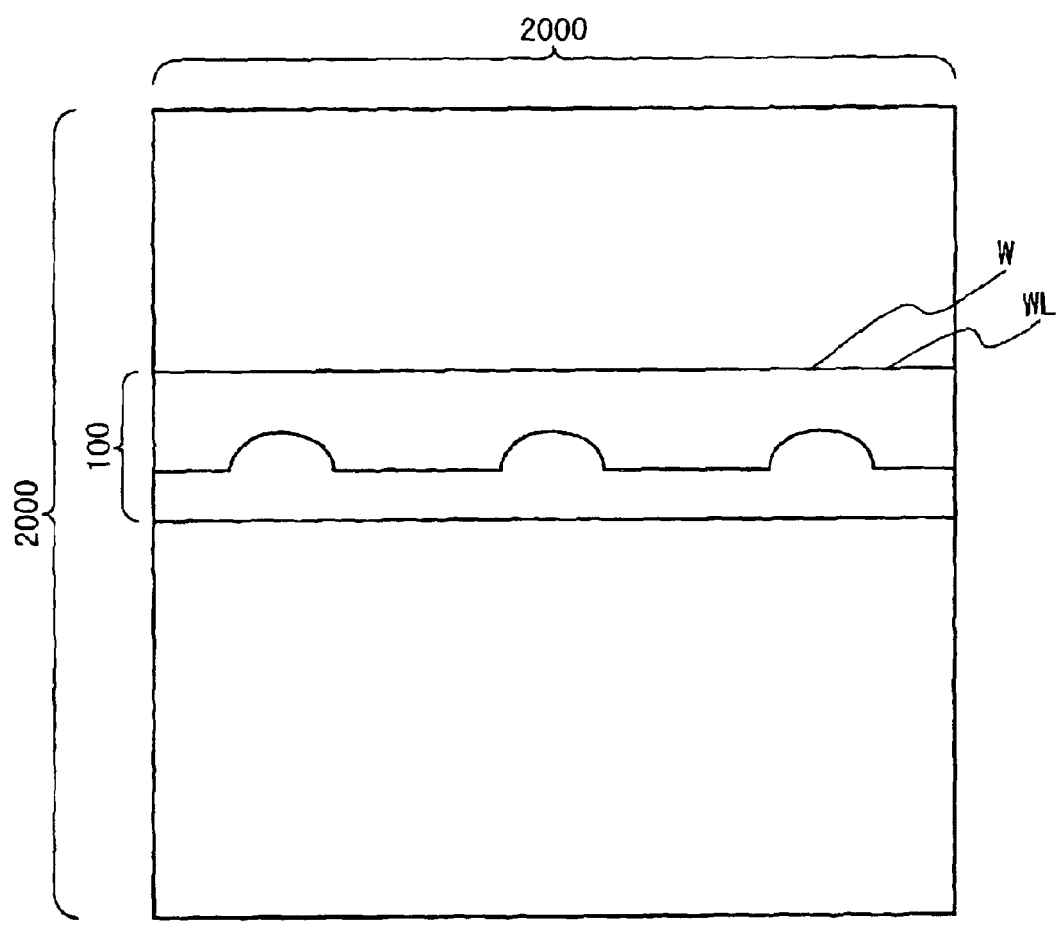
FIG. 12 is a view describing a partial scan done by a CCD sensor, in an embodiment of an apparatus for inspecting a semiconductor integrated circuit of the present invention.

As described later, the reason why the detection area DA is formed in the slender shape having the longitudinal direction in the same direction as the longitudinal direction of the slit shape of the laser beam LB although the CCD elements of the CCD sensor 42 are arrayed such that the pixel numbers of the line and the row are equal to each other (2000×2000) as shown in FIG. 12 is that the partial scan is carried out in the CCD sensor 42.

Figure 10B:
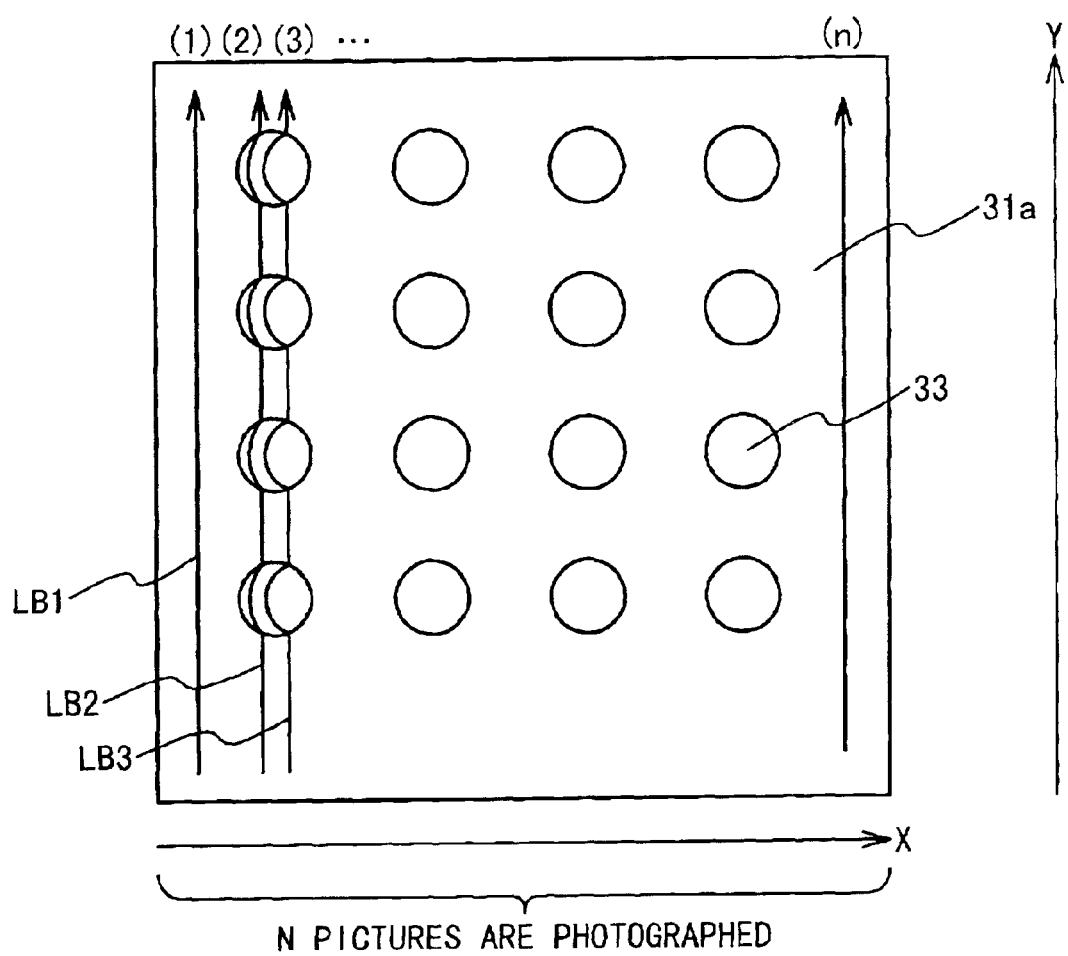
FIG. 10B is a plan view illustrating that the solder ball on the mount surface is scanned by a laser beam.

As indicated by a symbol (1) of FIG. 10B, a laser beam LB1 emitted to a flat substrate surface 31a (having no solder ball 33) is taken as a straight line M1 by the CCD sensor 42, as shown in FIG. 11A. This straight line M1 indicates the substrate surface 31a to which the laser beam LB1 is emitted.

As indicated by a symbol (2) of FIG. 10B, when the XY table is used to shift the laser light source 41 and the CCD sensor 42 in the X-direction, a laser beam LB2 is emitted to the lower portions of the solder balls 33, and it is taken as a line M2 composed of a straight line and a mountain in a shape of curve, which is small in height and width, in the CCD sensor 42, as shown in FIG. 11B. The straight portion of the line M2 indicates the substrate surface 31a to which the laser beam LB2 is emitted, and the mountain portion thereof indicates the surface of the solder ball 33 to which the laser beam LB2 is emitted.

As indicated by a symbol (3) of FIG. 10B, when the XY table is used to further shift the laser light source 41 and the CCD sensor 42 in the X-direction, a laser beam LB3 is emitted to the higher portions of the solder balls 33, and it is taken as a line M3 composed of a straight line and a mountain in a shape of curve, which is large in height and width, in the CCD sensor 42, as shown in FIG. 11C. The straight portion of the line M3 indicates the substrate surface 31a to which the laser beam LB3 is emitted, and the mountain portion thereof indicates the surface of the solder ball 33 to which the laser beam LB3 is emitted.

As shown in FIG. 10B, as for the substrate surface 31a of one IC chip 31 and the plurality of solder balls 33, similarly to the symbols (1) to (3), the XY table is used to shift the laser light source 41 and the CCD sensor 42 in the X-direction, and the laser beam LB is emitted to a total of n respective positions, and a total of n pictures are photographed.

The coordinate positions of X, Y at the emission positions of the laser beam LB at the respective measurement points in FIG. 10B are read out by the encoder installed to the XY table. The heights of the respective solder balls 33 at the respective measurement points in FIG. 10B are determined by the distance between the substrate surface 31a taken as the straight line and the maximum position of the curved mountain, in the respective pictures (the lines M1 to M3) of FIGS. 11A to 11C.

The light cutting method employed in this embodiment recognizes the entire shape and size of each solder ball 33, on the basis of each sectional shape when each solder ball 33 is sliced a plurality of times at a different height as shown in FIGS. 11A to 11C.

In this case, the apex position to determine the height of each solder ball 33 can not be specified in advance. Thus, as shown in FIG. 10B and FIGS. 11A to 11C, the laser beam LB is emitted to a plurality of positions of each solder ball 33, and the photograph of the CCD sensor 42 is done at the plurality of positions. Then, the maximum value of mountains obtained from respective photograph screens (FIGS. 11A to 11C) is defined as the height of the solder ball 33.

In this way, it is necessary to photograph each solder ball 33 a plurality of times. Thus, the scan time of the CCD sensor 42 necessary for the photographing for each time (the time required to obtain one picture) is desired to be short.

As mentioned above, the partial scan is done in the CCD sensor 42. This partial scan will be described below.

As shown in FIG. 12, the partial scan implies, for example, the operation for detecting only signal charges in the element regions of 100 (pixels)×2000 (pixels) in a CCD element region of 2000 (pixels)×2000 (pixels) of the CCD sensor 42, and the signal charges in the element regions besides it are not detected.

According to this partial scan, the scan to detect the signal charges is performed on only the region of 100 (pixels)×2000 (pixels). Thus, it is possible to attain the high speed operation, as compared with the case of scanning all the regions of 2000 (pixels)×2000 (pixels).

For example, it takes 400 mS to obtain one picture by scanning all the regions of 2000 (pixels)×2000 (pixels). However, it merely takes 20 mS to obtain one picture by scanning the region of 100 (pixels)×2000 (pixels).

In the BGA type IC chip 31, the height of the solder ball 33 is lower as compared with the width of the substrate of the IC chip 31 (the Y-direction of FIG. 10B). Thus, as shown in FIGS. 10A, 10B, if the solder balls 33 of the BGA type IC chip 31 are photographed for each row by the CCD sensor 42, the single photograph picture is the picture, which is long in a lateral direction, as shown in FIG. 12.

Thus, in the CCD element regions (2000×2000) of the CCD sensor 42 in which the longitudinal and lateral portions are composed of the same number of the pixels, the meaningful portion on the measurement is only the portion corresponding to the picture that is long in the lateral direction.

As mentioned above, while the positional relation between the CCD sensor 42 and the laser light source 41 shown in FIG. 9 is not changed, the entire laser sensor 40 is relatively shifted with respect to the IC chip 31. Thus, the laterally long picture at each of the plurality of measurement positions ((1) to (n) of FIG. 10B) to which the laser beam LB of the laser light source 41 is emitted is always photographed in the same region, among the CCD element regions (2000 (pixels)×2000 (pixels)) of the CCD sensor 42.

Thus, in the CCD sensor 42 in the embodiment, it is possible to carry out the partial scan for detecting only the signal charges in the regions of 100×2000 corresponding to the region, in which the laterally long picture is always photographed, in all the CCD element regions (2000×2000).

Here, let us consider the case that the solder balls of the BGA type IC chip are photographed for each row by the CCD sensor, in the above technique of Japanese Patent Publication (JP-B-Heisei, 6-103171) and the above technique of Japanese Laid Open Patent Application (JP-A-Heisei, 10-209227).

The techniques noted in both the gazettes employ the method in which the CCD sensor and the IC chip are fixed and the positions to which the linear light L is emitted are deviated in the order of the plurality of measurement positions of the IC chip.

For this reason, in the techniques of both the gazettes, the visual region of the fixed CCD sensor must cover all of the plurality of measurement positions ((1) to (n) of FIG. 10B) of the IC chip.

Moreover, the laterally long picture of each of the plurality of measurement positions to which the linear light L is emitted is not always photographed in the same region, in all the CCD element regions of the fixed CCD sensor. It is always photographed in a different region corresponding to the measurement position in all the CCD element regions of the fixed CCD sensor.

Thus, in the techniques of both the gazettes, it is extremely difficult to carry out the partial scan. In order to carry out the partial scan based on the techniques of both the gazettes, it is necessary to change the region on which the partial scan is performed, in all the CCD element regions, for example, such that the region in which the laterally long picture is photographed is responsible for and synchronous with the difference based on the measurement position.

In this embodiment, in order to match the height of the solder ball 33 of the measurement target or the like, for example, with the region of (100×2000) (indicated by an arrow W of FIG. 12) on which the partial scan is performed, it is done by considering the standard height from the substrate surface 31a of the solder ball 33 or the like. In this case, as necessary, the visual range can be adjusted by placing a lens (not shown) at a former stage of the CCD sensor 42.

Here, for example, a CCD sensor on the market can be used as the CCD sensor 42 for the partial scan for detecting only the signal charges in the element region W of 100 (pixels)×2000 (pixels). By the way, the CCD sensor in which all CCD element regions are composed of, for example, 100 (pixels)×2000 (pixels) is not sold on the market.

Also, the CCD sensor 42 for carrying out the partial scan can have the same configuration as the usually typical CCD sensor (which is not based on the partial scan manner) except the operation in which the region besides the region of 100×2000 to be scanned in all of the CCD element regions (2000×2000) is not scanned.

One usage method of the apparatus 10 will be described below.

At first, let us match the height of the solder ball 33 of the measurement target or the like, for example, with the region W of 100 (pixels)×2000 (pixels) on which the partial scan is performed. As mentioned above, it is possible to consider the standard height from the substrate surface 31a of the solder ball 33 or the like. Also, as necessary, it is possible to place the lens at the former stage of the CCD sensor 42.

When the plurality of solder balls 33 of the IC chip 31 are measured, even if the tallest solder ball 33 of them is photographed, both of the apex position of the solder ball 33 and the substrate surface 31a of the IC chip 31 must be photographed within the range W on which the partial scan is performed. This is because the height of the solder ball 33 can be measured, only if both of the apex position of the solder ball 33 and the substrate surface 31a of the IC chip 31 are photographed.

Moreover, the apex position of the solder ball 33 and the substrate surface 31a of the IC chip 31 are adjusted such that they are as close as possible to each other, while the necessary margin is reserved, with respect to an outline WL of the partially scanned range W, when the tallest solder ball 33 of them is photographed within the partially scanned range W. This is done in order to reserve the higher resolution.

In this way, in the apparatus 10, the apex position of the expected tallest solder ball 33 and the substrate surface 31a of the IC chip 31 are adjusted such that they are as close as possible to each other, with respect to the outline WL of the partially scanned range W. This adjustment brings about the following problem.

If the tray (including an in-tray and a JEDEC tray) 93 containing the IC chip 31 is curved, or if the package of the IC chip 31 is defective, there may be the case of the change in the positional relation (distance) between the laser sensor 40 (the laser light source 41 and the CCD sensor 42) and the z-direction (height direction) of the IC chip 31. This may result in the fear that the apex position of the solder ball 33 or the substrate surface 31a of the IC chip 31 is out of the partially scanned range W and the height of the solder ball 33 can not be measured.

The apparatus 10 employs the following counter-plan in order to previously avoid the occurrence of the above-mentioned problem that is easily susceptible to occur in the partially scanning method.

As shown in FIGS. 11A to 11C, when the picture in the partially scanned range W is photographed, the distribution in the height direction (Z-direction) of the dot number implying the detection of the value of one bit indicative of the light emission is detected is measured in each photograph picture.

Figure 13:
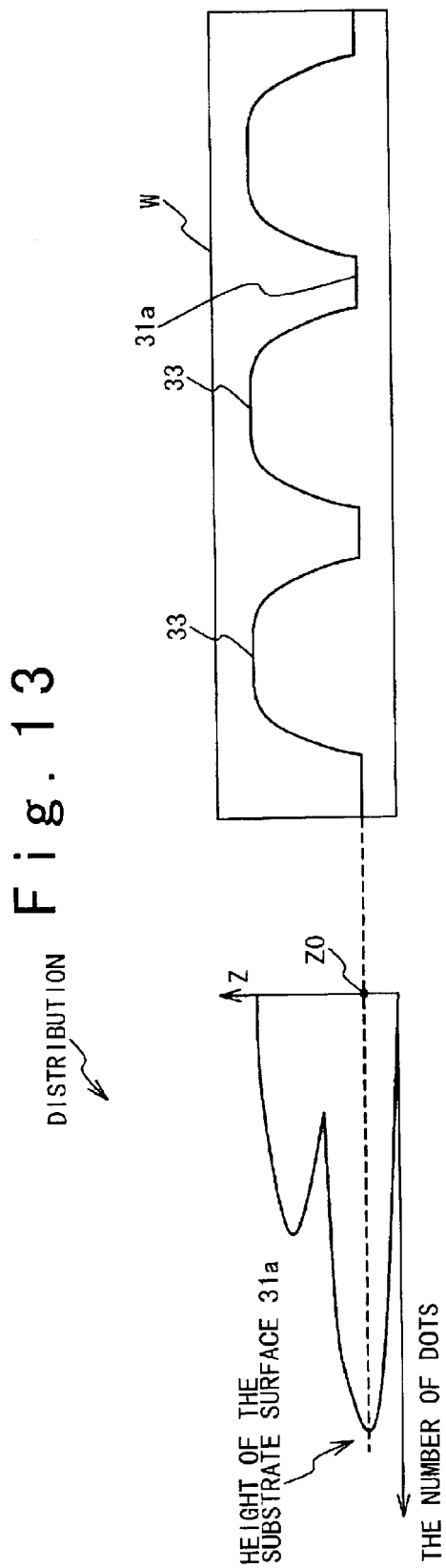
FIG. 13 is a distribution view showing a relation between a height direction of a photograph picture and a dot number indicating that a light is emitted, corresponding to a photograph picture, in an embodiment of an apparatus for inspecting a semiconductor integrated circuit of the present invention.

For example, the photograph picture (the partially scanned range W) shown in FIG. 13 exhibits the distribution shown in FIG. 13. As shown in FIG. 13, the number of dots of the height corresponding to the substrate surface 31a is maximum in the photograph picture (the partially scanned range W) in FIG. 13. A height Z0 in FIG. 13 corresponds to the height of the substrate surface 31a, the moment the picture (the partially scanned range W) of FIG. 13 is photographed.

As shown in FIGS. 11A to 11C, the dot number of the height corresponding to the substrate surface 31a is maximum even in any of the photograph pictures M1 to M3. Thus, if measuring the distribution (FIG. 13) with regard to each of the plurality of photograph pictures photographed by the CCD sensor 42 and then measuring the change in the height (Z) corresponding to the maximum dot number in accordance with the measured result, it is possible to detect the change in the distance between the laser sensor 40 and the substrate surface 31a caused by the curvature of the tray 93 and the like. Here, the curvature of the tray 93 is, for example, about 600 μm, and the height of the solder ball 33 is, for example, also about 600 μm.

Figure 14:
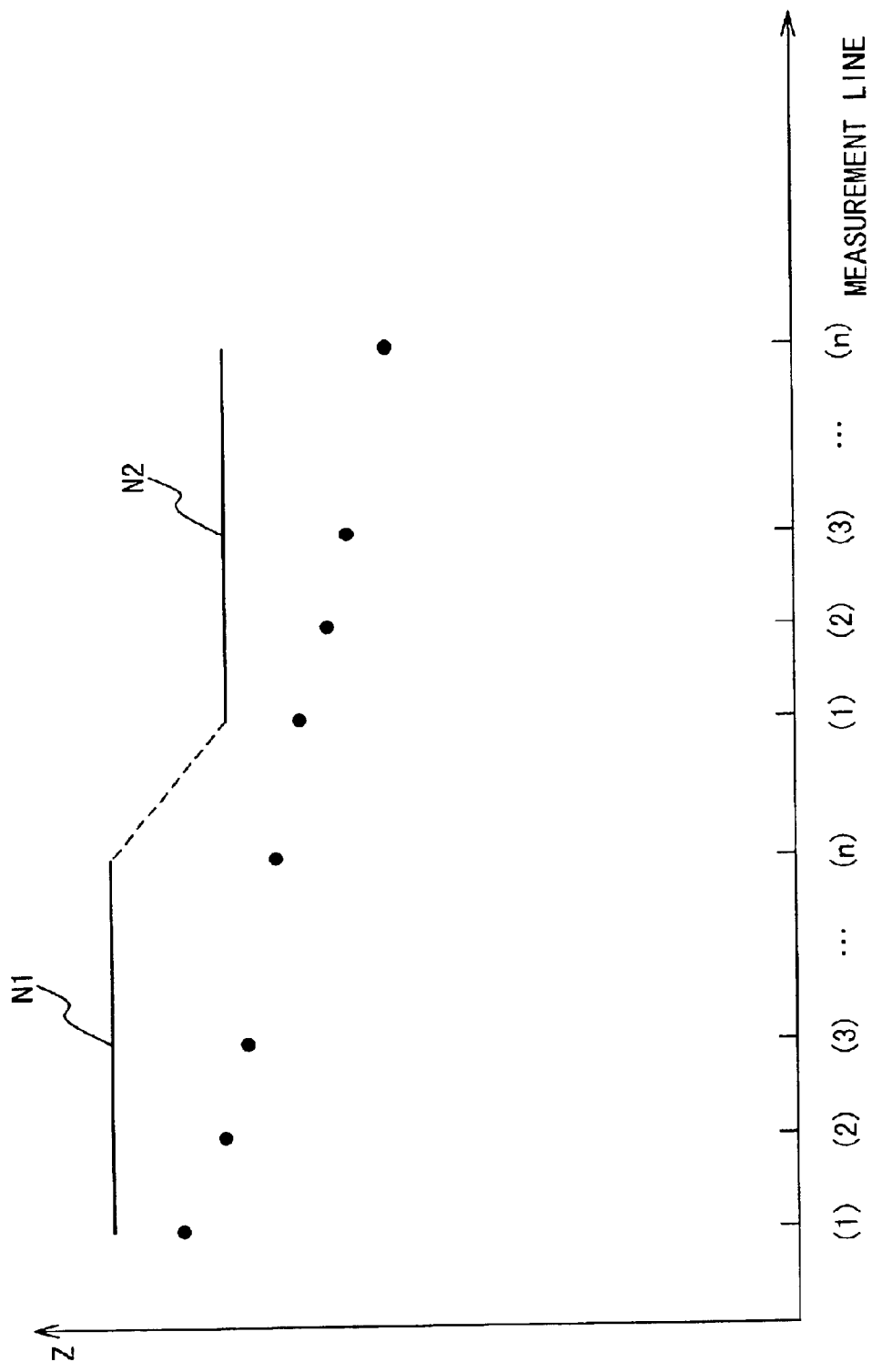
FIG. 14 is a graph view showing a height of a mount surface in each measurement line, in an embodiment of an apparatus for inspecting a semiconductor integrated circuit of the present invention.

FIG. 14 shows the heights Z of the substrate surfaces 31a with regard to the plurality of photograph pictures detected in accordance with the distribution of FIG. 13. In FIG. 14, the vertical axis indicates the height Z of the substrate surface 31a, and the horizontal axis indicates the order in which the photographing operation is done (the measurement line).

(1), (2), (3), . . . (n) on the horizontal axis shown in FIG. 14 correspond to (1), (2), (3), . . . (n) shown in FIG. 10B, respectively. In the horizontal axis of FIG. 14, the items on and after (1) at the second photograph indicate the respective measurement lines of a next IC chip 31.

That is, (1) on the horizontal axis of FIG. 14 corresponds to the photographed result (refer to FIG. 11A) when the laser beam LB1 is emitted to the position (1) of FIG. 10B, and a value of a vertical axis Z corresponding to the horizontal axis (1) of FIG. 14 indicates the height of the substrate surface 31a at the position (1) of FIG. 10B when the photographing operation is done. A height Z of the substrate surface indicated on the vertical axis of FIG. 14 indicates an attribute height (for example, a height from a floor on which the apparatus 10 is installed).

FIG. 14 indicates that the heights of the substrate surfaces 31a of the respective measurement lines (1), (2), (3) . . . in one IC chip 31 are gradually lower towards the arrow X-direction of FIG. 10B. This is, for example, because the tray 93 containing the IC chip 31 is curved.

Figure 16:
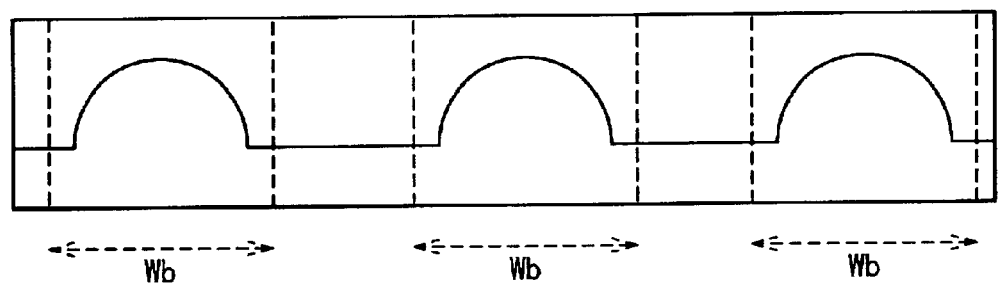
FIG. 16 is a view describing a partial scan when a CMOS sensor is used, in a third variation of an embodiment of an apparatus for inspecting a semiconductor integrated circuit of the present invention.

In order to previously avoid the occurrence of the above-mentioned problem that the height of the solder ball 33 can not be measured since the apex position of the solder ball 33 or the substrate surface 31a of the IC chip 31 is out of the partially scanned range W because of the curvature of the tray 93 and the like, the apparatus 10 shifts the laser light source 41 and the CCD sensor 42 in the Z (height) direction, while the positional relation between them shown in FIG. 16 is held, at real time, on the basis of the respective values Z on the vertical axis of FIG. 14.

When the measurement lines (1), (2) of FIG. 10B are photographed to thereby obtain the pictures shown in FIGS. 11A, 11B, if the drop in the height of the substrate surface 31a between the photographing of the measurement line (1) and the photographing of the measurement line (2) is detected as shown in FIG. 14, the heights of the laser light source 41 and the CCD sensor 42 are dropped so as to compensate for the change in the height, at real time.

The control of the heights of the laser light source 41 and the CCD sensor 42 done at this time drops the heights of the laser light source 41 and the CCD sensor 42 so that the height of the substrate surface 31a becomes a predetermined height within the partially scanned range W, when a next measurement line (3) or a measurement line on and after (3) is photographed.

As mentioned above, instead of the method of controlling the heights of the laser light source 41 and the CCD sensor 42 at the real timing, the heights of the laser light source 41 and the CCD sensor 42 can be controlled at the timing when the measurement target is shifted to a next IC chip 31.

In FIG. 14, a symbol N1 indicates the heights of the laser light source 41 and the CCD sensor 42 when the first IC chip 31 is measured, and a symbol N2 indicates the heights of the laser light source 41 and the CCD sensor 42 when the next IC chip 31 is measured.

Also, as shown in FIG. 14, when the heights Z of the substrate surfaces 31a on the respective measurement lines are changed at the substantially identical inclination over the plurality of continuous IC chips 31, it is imagined that the portions of the tray 93 are entirely inclined at the substantially identical inclination. Thus, the height Z of the non-measured measurement line or the substrate surface 31a of the non-measured IC chip 31 can be expected to some degree, in accordance with the imagination and the like. Then, the heights of the laser light source 41 and the CCD sensor 42 can be controlled in accordance with the expected result.

A variation in this embodiment will be described below with reference to FIG. 15.

In the above-mentioned embodiment, the partial scan of the CCD sensor 42 is done such that the range W of 100 (pixels)×2000 (pixels) shown in FIG. 12 is scanned by a non-interlace method. On the contrary, the partial scan of the CCD sensor 42 according to the variation is done such that a range Wa of 200 (pixels)×2000 (pixels) shown in FIG. 15 is scanned by an interlace method.

Figure 15:
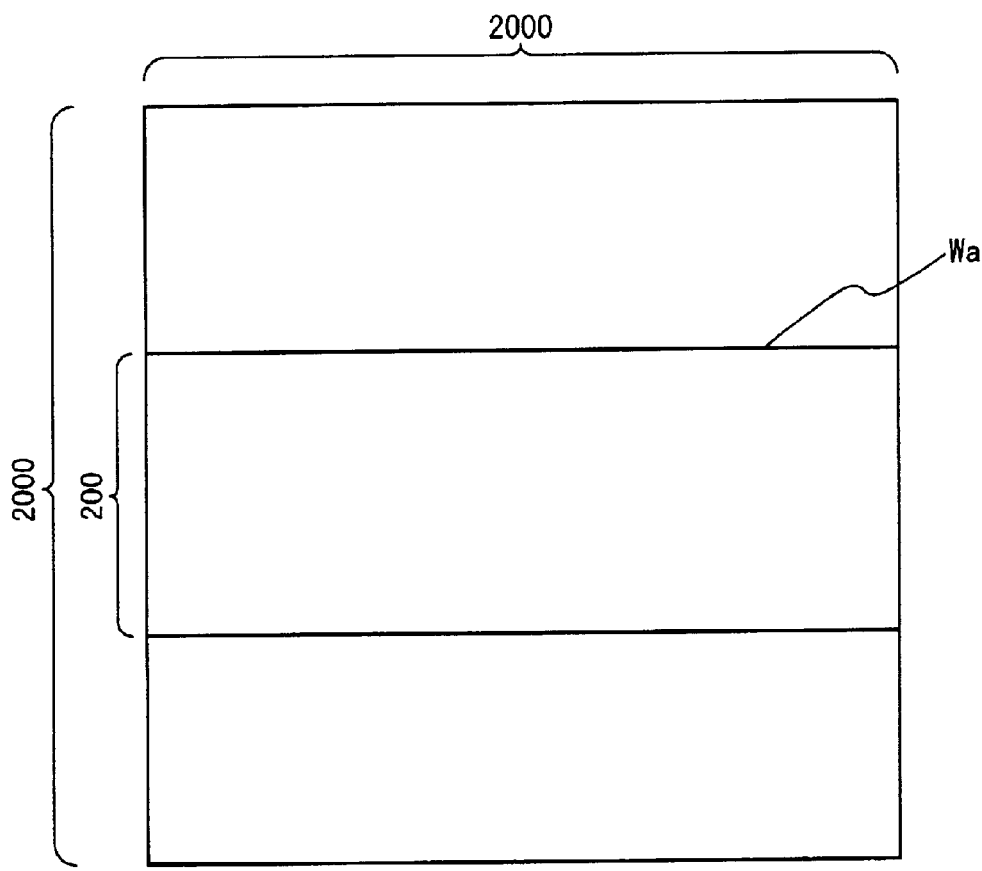
FIG. 15 is a view describing an interlace method and a partial scan employed in a variation of an embodiment of an apparatus for inspecting a semiconductor integrated circuit of the present invention.

That is, when the measurement line (1) of FIG. 10B is photographed, a signal is written to pixels corresponding to 100 lines on odd-numbered lines within the range Wa of FIG. 15.

When the measurement line (2) of FIG. 10B is photographed, a signal is written to pixels corresponding to 100 lines on even-numbered lines within the range Wa of FIG. 15.

Next, when the measurement line (3) of FIG. 10B is photographed, a signal is written to the pixels corresponding to the 100 lines on the even-numbered lines within the range Wa of FIG. 15.

The scanning based on the interlace method is meaningful since the partial scan is done in the CCD sensor 42, as described below.

In the CCD sensor, instead of the partial scan, if all of the CCD element regions (2000×2000) are scanned, in the case of the conventional typical interlace method, a signal is written to pixels corresponding to 1000 lines on odd-numbered lines at a first scan, and a signal is written to pixels corresponding to 1000 lines on even-numbered lines at a next scan. Then, one picture (2000×2000) is generated in the two scans.

On the contrary, in the interlace scan when the partial scan is done in the CCD sensor 42, the generation of the picture for one measurement line is completed at one scan on the odd-number or even-numbered line. Thus, the combination of the partial scan and the interlace scan enables the picture to be generated in a shorter time than that of the case when the partial scan is not done.

Moreover, the following effect can be provided when the interlace scan is done in the CCD sensor 42 for carrying out the partial scan.

Here, similarly to the above-mentioned case, at first, when the measurement line (1) of FIG. 10B is photographed, the signal is written to the pixels corresponding to the 100 lines on the odd-numbered lines in the range Wa of FIG. 15. When the measurement line (2) of FIG. 10B is photographed, the signal is written to the pixels corresponding to the 100 lines on the even-numbered lines in the range Wa of FIG. 15. Next, when the measurement line (3) of FIG. 10B is photographed, the signal is written to the pixels corresponding to the 100 lines on the odd-numbered lines in the range Wa of FIG. 15.

In the above-mentioned embodiment in which the non-interlace scan is done, when each measurement line is photographed, the signal is always written to the range W of 100 (pixels)×2000(pixels) of FIG. 12. Thus, in the CCD element of the range W, one cycle from its reset to the detection of the signal must be carried out within the time between the photographing of a certain measurement line and the photographing of a next measurement line.

On the contrary, in this variation in which the interlace scan is done, the pixels corresponding to the 100 lines on the odd-numbered lines of the range Wa of FIG. 15 are not used until the photographing of the measurement line (3), after they are used for photographing the measurement line (1) of FIG. 10B. Thus, the CCD elements in the range Wa are sufficient if the one cycle from the reset to the detection of the signal is done within the period between the photographing of a certain measurement line and the photographing of the measurement line two measurement lines later.

As mentioned above, in this variation in which the interlace scan is done, it is possible to make the time of the one cycle longer. Thus, it is possible to surer carry out the reset operation and the signal detection operation, and thereby possible to improve the sensibility and the detection ability.

Since the partial scan is done, all the pixels (2000×2000) of all the CCD element regions are divided into the pixels that are used for a signal detection in photographing and the pixels that are not used for the signal detection in the photographing. If the pixels that are not used for the signal detection in the photographing are used for a signal detection in photographing next to the photographing, it is possible to increase the time of one cycle until the signal detection after the reset of each pixel.

Figure 17:
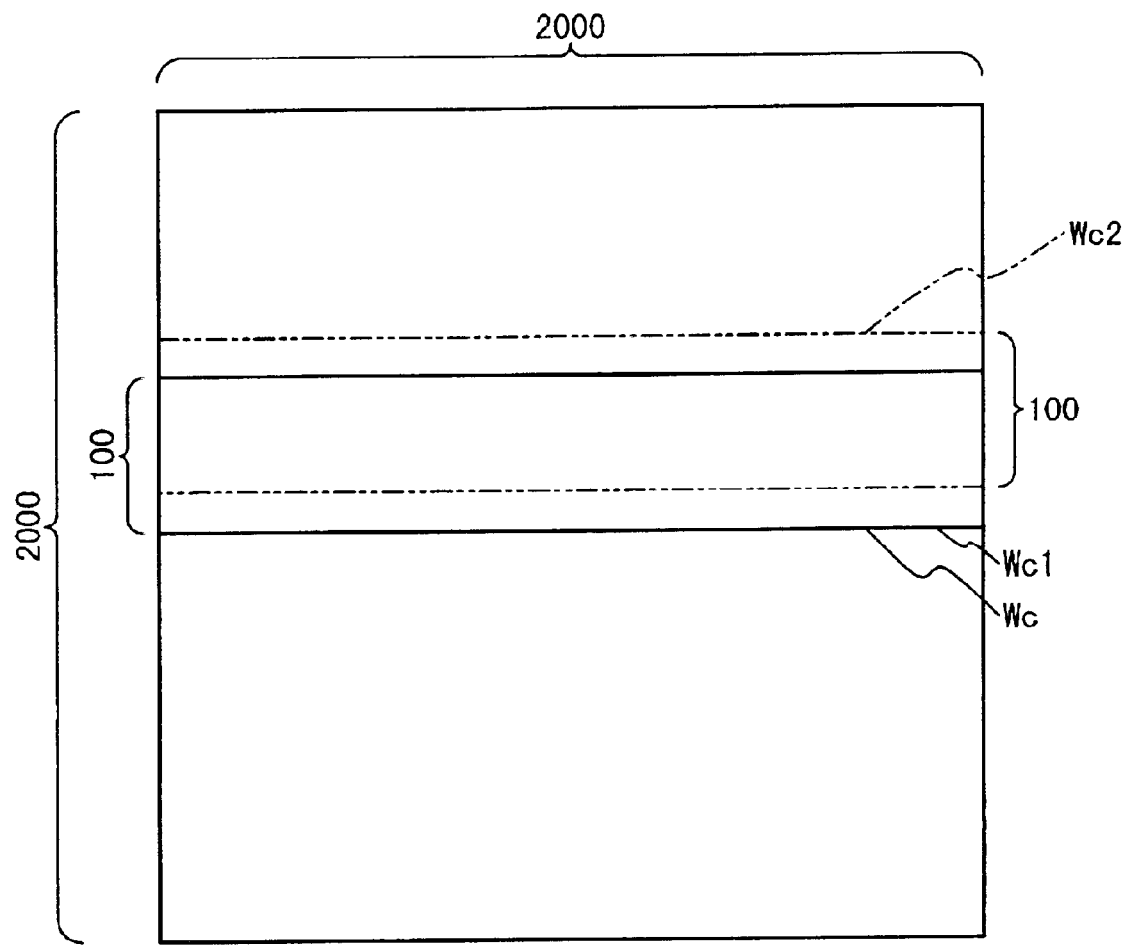
FIG. 17 is a view describing a partial scan employed in a second variation of an embodiment of an apparatus for inspecting a semiconductor integrated circuit of the present invention.

A second variation of the above-mentioned embodiment will be described below with reference to FIG. 17.

As the CCD sensor 42 in this variation, the sensor is used that can change a range Wc on which the partial scan is performed.

In the above-mentioned embodiment, when the measurement lines (1), (2) of FIG. 10B are photographed to thereby generate the pictures shown in FIGS. 11A, 11B, if the change in the height of the substrate surface 31a between the photographing of the measurement line (1) and the photographing of the measurement line (2) is detected in accordance with the result shown in FIG. 14, the height of the laser sensor 40 is adjusted so as to compensate for the change in the height, for each change in the IC chip 31 of the measurement target or at real time.

In this variation, instead of the height adjustment of the laser sensor 40, the partially scanned range Wc of the CCD sensor 42 is changed (refer to symbols Wc1, Wc2). In this case, the partially scanned range Wc can be adjusted such that the position of the substrate surface 31a always corresponds to a predetermined position in the partially scanned range Wc, even if the height of the substrate surface 31a is changed.

Accordingly, it is possible to previously avoid the situation that the height of the solder ball 33 can not be measured since the apex position of the solder ball 33 or the substrate surface 31a of the IC chip 31 is out of the partially scanned range Wc because of the curvature of the tray 93 and the like.

A third variation of the above-mentioned embodiment will be described below.

In this variation, a CMOS sensor is used instead of the CCD sensor 42 for the 3D measurement. Its merit will be described below.

The CCD sensor can only attain the higher speed of the signal detection by performing the partial scan on the region in which the scanning number of all the CCD elements (for example, 2000×2000) is reduced (the region in which the pixel number on one side is reduced, for example, the range W of 100×2000), because of its property.

On the contrary, in the CMOS sensor, the signal can be also detected only from a desirable region (a region in which the pixel number is reduced not only on one side but also on the other side, for example, a range of 100×100) in all of the CMOS elements (for example, 2000×2000). That is, in the CMOS sensor, a free degree to set a range from which a signal is taken away is higher than that of the CCD sensor.

By the way, the CCD camera and the CMOS sensor are both cheaper than a measuring system using a PSD (Photo Sensing Diode), due to the structures of their devices.

In the Y-direction of FIG. 10B, the position at which the solder ball 33 is placed is substantially known in advance. Thus, in the CMOS sensor in this variation, the range from which the signal is taken away can be set at a range Wb indicated by a dashed line of FIG. 16.

Moreover, the higher speed of the signal detection can be attained by setting a spot range, in which the solder ball 33 can be photographed, as the range Wb from which the signal of the CMOS sensor for the 3D measurement is taken away, after the position and the size of the solder ball 33 in the IC chip 31 are determined, in accordance with the photographed result by the CCD camera sensor 90 for the 2D measurement.

A fourth variation in the above-mentioned embodiment will be described below.

Figure 18:
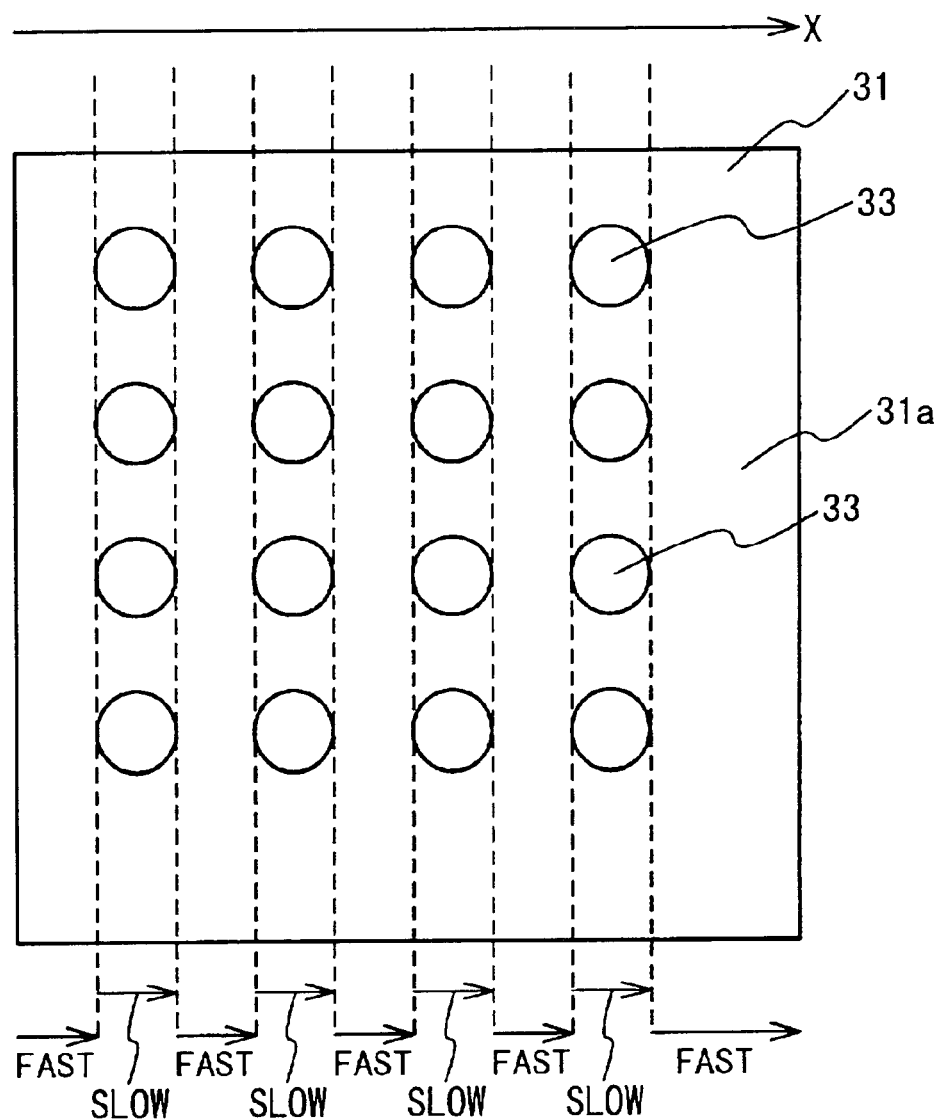
FIG. 18 is a view describing a shift speed of a laser sensor employed in a fourth variation of an embodiment of an apparatus for inspecting a semiconductor integrated circuit of the present invention.

When the laser beam LB is emitted to the measurement position (measurement line) at which the solder ball 33 exists after the position and the size of the solder ball 33 in the IC chip 31 are determined as shown in FIG. 18 in accordance with the photographed result by the CCD camera sensor 90 for the 2D measurement, the shifting speed to the X-direction of the laser sensor 40 done by the XY sensor is made slower, as compared with the case of the emission to the measurement position (substrate surface 31a) at which the solder ball 33 does not exist.

The shifting speed is controlled as mentioned above, and a large number of photographs are carried out at a shorter pitch, at the position of the existence of the solder ball 33. Thus, it is possible to further accurately measure the height of the solder ball 33, which is important in this measurement. Together with it, the higher speed of the measurement can be attained by reducing the number of photographs only for the substrate surface 31a, which is relatively low in importance.

A fifth variation of the above-embodiment will be described below.

Each of the CCD sensor 42 and the CCD camera sensor 90, in which wave lengths used for the 3D measurement and the 2D measurement are changed, can include a filter for receiving only a light having a desirable wave length. Thus, there is no influence between the mutual lights.

Moreover, one camera can serve as the CCD sensor for the 3D measurement and the CCD camera sensor for the 2D measurement, and the 2D measurement and the 3D measurement can be alternately carried out.

Figure 19:
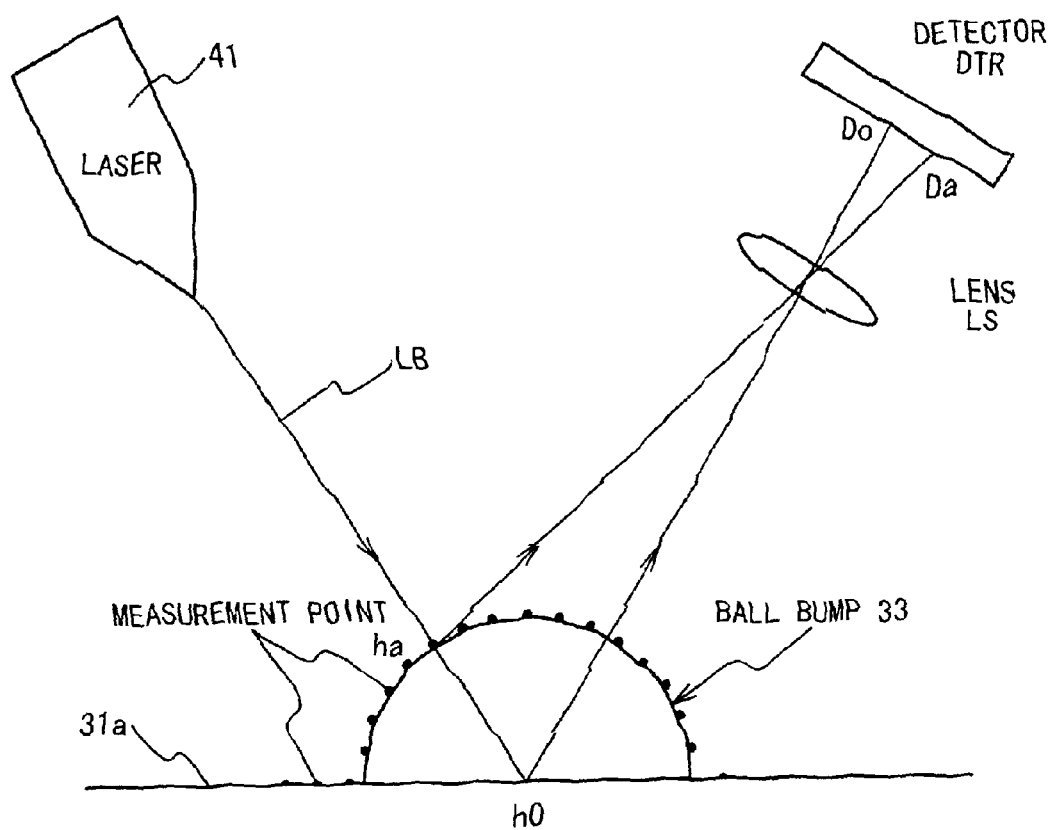
FIG. 19 is a view describing a measuring principle of a light cutting method that can be employed in an embodiment of an apparatus for inspecting a semiconductor integrated circuit of the present invention.

By the way, the above-mentioned embodiment employs the method of carrying out the 3D measurement by using the light cutting method. However, the following method can be employed. Its measurement principle will be described below with reference to FIG. 19.

The laser beam LB emitted from the laser light source 41 is reflected on the surface of the solder ball 33 or the substrate surface 31a, and it is sent through a lens LS to a detector DTR. Here, the light reflected on a surface ha of the solder ball 33 produces an image Da on the detector. If the ball 33 is absent, the beam is reflected on a substrate surface h0 and similarly sent through the lens LS to produce an image D0 on the detector DTR.

The result after an angular compensation is performed on a difference between the two points Da, D02 becomes a height (Z) of the surface ha of the solder ball 33. Values of the respective measurement points X, Y at this time are read out from the encoder placed on the XY table. The measurement points are obtained in the shape of matrix dot at a predetermined pitch on the substrate. Then, the measurement values of X, Y and Z are determined for all of the measurement points, and they are sent to an operational unit. The operational unit converts into 3D data in accordance with a predetermined algorism.

As mentioned above, the inspector of the semiconductor integrated circuit in this embodiment can quickly measure the cubic body such as the solder ball 33 or the like. It is possible to shorten the time required to obtain the photograph picture of the cubic body. It is possible to shorten the scan time of the photographing unit for obtaining the photograph picture of the cubic body. Since the scan width can be made narrow, the data amount can be reduced over the conventional technique. Thus, it is also possible to shorten the calculation time.

Also, according to the inspector of the semiconductor integrated circuit in this embodiment, when the feeding unit such as the tray 93 containing the cubic body such as the solder ball 33 or the like or the tray 93 is shifted, even if the shifting unit, the feeding unit for feeding the tray 93 and the package unit of the IC chip 31 have the trouble such as the curvature and the like, it is possible to automatically cancel the bad influence caused by the trouble. It is possible to cancel the bad influence caused by the trouble at real time.

By the way, in the above-mentioned explanation, the contents noted in the embodiments and the contents noted in the variations can be suitably combined.

According to the inspector of the semiconductor integrated circuit of the present invention, the cubic body such as the solder ball and the like can be measured at the low cost and at the high speed. It can be designed as the simple apparatus configuration without any usage of the detection mechanism of the laser sensor (scanner).

What is claimed is:

1. A semiconductor integrated circuit inspecting apparatus inspecting a terminal provided on a mount surface of a semiconductor integrated circuit, comprising:
    a light emitter emitting a linear light obliquely to said mount surface;
    a photographing unit photographing said mount surface to which said light is emitted to output a photograph signal;
    an inspector inspecting said terminal in accordance with said photograph signal, and
    wherein said photographing unit has N (N is a positive integer) photographing elements, and
    wherein said photograph signal is outputted respectively only from M (M is a positive integer smaller than said N) photographing elements of said N photographing elements.

2. The semiconductor integrated circuit inspecting apparatus according to claim 1, wherein only scanning lines corresponding to said M photographing elements of said N photographing elements are scanned such that said photographing unit outputs photograph signals.

3. The semiconductor integrated circuit inspecting apparatus according to claim 1, wherein said photographing unit has N (=n lines×l rows) (n and l are positive integers, respectively) photographing elements, and
    wherein only scanning lines corresponding to M (=m×l rows) (m is a positive integer smaller than said n) photographing elements of said photographing elements of n lines×l rows are scanned such that said photographing unit outputs photographing signals.

4. The semiconductor integrated circuit inspecting apparatus according to claim 1, wherein said light emitter and said photographing unit constitutes a sensor, and wherein when regions on said mount surface to which said light is emitted are changed, one of said sensor and said semiconductor integrated circuit is relatively shifted with respect to the other one of said sensor and said semiconductor integrated circuit such that said M photographing elements can photograph said regions to which said light is emitted.

5. The semiconductor integrated circuit inspecting apparatus according to claim 4, further comprising:
a first controller controlling a distance between said sensor and said semiconductor integrated circuit,
a calculator calculating a height of said mount surface in accordance with said photograph signal; and
wherein said first controller controls said distance in accordance with said calculated height of said mount surface.

6. The semiconductor integrated circuit inspecting apparatus according to claim 5, wherein said first controller controls said distance such that said M photographing elements can photograph said mount surface to which said light is emitted, when said height of said mount surface is changed.

7. The semiconductor integrated circuit inspecting apparatus according to claim 4, further comprising:
a two-dimensional measurement photographing unit photographing a flat shape of said mount surface; and
a shifting unit shifting said two-dimensional measurement photographing unit and said sensor with respect to said semiconductor integrated circuit.

8. The semiconductor integrated circuit inspecting apparatus according to claim 1, further comprising:
a calculator calculating a height of said mount surface, in accordance with said photograph signal.

9. The semiconductor integrated circuit inspecting apparatus according to claim 8, wherein said calculator determines a relation between the number of dots indicative of the emission of said light and a position in a height direction of said semiconductor integrated circuit, in a photograph picture photographed by said M photographing elements to calculate a height of said mount surface, in accordance with said relation.

10. The semiconductor integrated circuit inspecting apparatus according to claim 8, further comprising:
a second controller controlling said photographing elements such that said M photographing elements outputting photograph signals of said N photographing elements are changed, and
wherein said second controller controls said photographing elements such that said M photographing elements are changed, in accordance with said calculated height of said mount surface.

11. The semiconductor integrated circuit inspecting apparatus according to claim 1, wherein said photographing element is a CMOS photographing element or a CCD photographing element.

12. The semiconductor integrated circuit inspecting apparatus according to claim 11, wherein CMOS photographing elements or CCD photographing elements of said N are arranged in a shape of a matrix composed of p lines and q rows (each of p and q is a positive integer), and wherein photograph signals are outputted only from said CMOS photographing elements or CCD photographing elements in a range of (p-$\alpha$) lines and (q-$\beta$) rows (said $\alpha$ is a positive integer smaller than said p, and said $\beta$ is a positive integer smaller than said q).

13. The semiconductor integrated circuit inspecting apparatus according to claim 1, wherein an angle between an optical axis of said light emitter and an axis line of said photographing unit is about 90 degrees.

14. The semiconductor integrated circuit inspecting apparatus according to claim 1, wherein an axis line of said photographing unit substantially coincides with an optical axis of a light reflected from said mount surface to which said light is emitted.

15. The semiconductor integrated circuit inspecting apparatus according to claim 1, wherein when positions of said mount surface to which said light is emitted are changed from a first position to a second position, photograph signals in which said first position is photographed are outputted only from a first photographing element group of said M photographing elements of said N photographing elements, and said photograph signals in which said second position is photographed are outputted only from a second photographing element group of said M photographing elements different from said first photographing element group of said N photographing elements.

16. The semiconductor integrated circuit inspecting apparatus according to claim 1, wherein said semiconductor integrated circuit is a BGA, and wherein said terminal is a solder ball, and wherein said inspector measures a height of said solder ball in accordance with said photograph signal.

17. A method of inspecting a semiconductor integrated circuit, which inspects a terminal provided on a mount surface of a semiconductor integrated circuit, comprising:

(a) providing a photographing unit having N (N is a positive integer) photographing elements;

(b) detecting a position of said terminal on said mount surface;

(c) obliquely emitting a linear light to said mount surface;

(d) relatively shifting an emission target of said light and said mount surface at a set speed such that said light is emitted to each of a plurality of positions of said mount surface;

(e) photographing by said photographing unit a region on said mount surface to which said light is emitted to output a photograph signal from said photographing unit; and (f) inspecting said terminal in accordance with said photograph signal, and wherein a plurality of said photograph signals is outputted from only M (M is a positive integer smaller than said N) photographing elements of said N photographing elements, and wherein said set speed when said light is emitted to said terminal is set to be higher as compared with a case when said light is not emitted to said terminal, based on a result of said (b).

18. The method of inspecting a semiconductor integrated circuit according to claim 17, wherein a combination of said (c), (d), (e) and (f) constitutes a light cutting method.

19. A method of inspecting a semiconductor integrated circuit, which inspects a terminal provided on a mount surface of a semiconductor integrated circuit, comprising:

(g) providing a photographing unit having N (N is a positive integer) CMOS photographing elements or CCD photographing elements arranged in a shape of a matrix composed of p lines and q rows (each of p and q is a positive integer);

(h) detecting a position of said terminal on said mount surface;

(i) obliquely emitting a linear light to said mount surface;

(j) photographing by said photographing unit a region on said mount surface to which said light is emitted to output a photograph signal from said photographing unit; and (k) inspecting said terminal in accordance with said photograph signal, and wherein a plurality of photograph signals are outputted from only M (M is a positive integer smaller than said N) CMOS photographing elements or CCD photographing elements in a range of (p-α) lines and (q-β) rows (said α is a positive integer smaller than said p, and said β is a positive integer smaller than said q) of said N CMOS photographing elements or CCD photographing elements, and wherein said range of said (p-α) lines and (q-β) rows is set to include a single one of said terminal in accordance with said result of said (h).

20. The method of inspecting a semiconductor integrated circuit according to claim 19, wherein a combination of said (i), (j) and (k) constitutes a light cutting method.

* * * * *